(12) United States Patent
Walish et al.

(10) Patent No.: US 12,702,477 B2
(45) **Date of Patent: *Aug. 11, 2026**

(54) UTERINE MANIPULATOR WITH NEUTRAL RETURN ELECTRODE

(71) Applicant: GYRUS ACMI, INC., Westborough, MA (US)

(72) Inventors: Judy L. Walish, Boston, MA (US); Dennis G. Lamser, Marlborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,049

(22) Filed: Apr. 18, 2024

(65) Prior Publication Data

US 2024/0261021 A1 Aug. 8, 2024

Related U.S. Application Data

(62) Division of application No. 17/493,437, filed on Oct. 4, 2021, now Pat. No. 11,998,267.

(Continued)

(51) Int. Cl.

*A61B 18/12* (2006.01)
*A61B 18/14* (2006.01)

(Continued)

(52) U.S. Cl.

CPC .......... *A61B 18/16* (2013.01); *A61B 18/1206* (2013.01); *A61B 18/1482* (2013.01);

(Continued)

(58) Field of Classification Search

CPC ........... A61B 17/42; A61B 2017/4225; A61B 18/1206; A61B 18/1482; A61B 18/1485; A61B 18/16; A61B 2018/00202; A61B 2018/00273; A61B 2018/00559; A61B 2018/00601; A61B 2018/00773;

(Continued)

(56) References Cited

U.S. PATENT DOCUMENTS 6,139,538 A 10/2000 Houghton et al.
6,258,085 B1 7/2001 Eggleston (Continued)

FOREIGN PATENT DOCUMENTS

CN 114288010 A 4/2022
CN 114288010 1/2026

(Continued)

OTHER PUBLICATIONS

"U.S. Appl. No. 17/493,437, Non Final Office Action mailed Oct. 5, 2023", 12 pgs.

(Continued)

*Primary Examiner* — Khadijeh A Vahdat
(74) *Attorney, Agent, or Firm* — Schwegman Lundberg & Woessner, P.A.

(57) ABSTRACT

A uterine manipulator including an elongate shaft having a distal portion configured to be inserted into a uterus through a lumen of a cervix, and a return electrode coupled to the elongate shaft. The return electrode is configured to be electrically coupled to an electrosurgical generator.

19 Claims, 10 Drawing Sheets

Related U.S. Application Data

(60) Provisional application No. 63/089,147, filed on Oct. 8, 2020.

(51) Int. Cl.
*A61B 18/16* (2006.01)
*A61B 34/00* (2016.01)
*A61B 18/00* (2006.01)

(52) U.S. Cl.
CPC .... *A61B 34/70* (2016.02); *A61B 2018/00601* (2013.01); *A61B 2018/00773* (2013.01)

(58) Field of Classification Search
CPC A61B 2018/00827; A61B 2018/00869; A61B 2018/00875; A61B 2018/00892; A61B 2018/162; A61B 2018/165; A61B 2090/065; A61B 34/70
See application file for complete search history.

(56) References Cited

U.S. PATENT DOCUMENTS

| | | | | |
|---|---|---|---|---|
| 7,850,684 | B2 | 12/2010 | Marshall et al. | |
| 8,323,278 | B2 | 12/2012 | Brecheen et al. | |
| 8,608,738 | B2 | 12/2013 | Brecheen et al. | |
| 9,144,454 | B2 | 9/2015 | Batchelor et al. | |
| 10,034,687 | B2 | 7/2018 | Brecheen et al. | |
| 11,998,267 | B2 | 6/2024 | Walish et al. | |
| 2002/0188242 | A1 | 12/2002 | Wu | |
| 2010/0191238 | A1 | 7/2010 | Kornerup | |
| 2012/0143210 | A1* | 6/2012 | Brecheen | A61B 17/42 606/119 |
| 2012/0323079 | A1 | 12/2012 | Bakare et al. | |
| 2013/0245728 | A1 | 9/2013 | Galen et al. | |
| 2016/0022353 | A1* | 1/2016 | Forsyth | A61B 34/10 606/34 |
| 2018/0325575 | A1 | 11/2018 | Begg et al. | |
| 2019/0059982 | A1* | 2/2019 | Smith | A61B 18/14 |
| 2019/0083133 | A1 | 3/2019 | Prior | |
| 2019/0167306 | A1 | 6/2019 | Brecheen et al. | |
| 2019/0269451 | A1 | 9/2019 | Begg | |
| 2020/0261178 | A1 | 8/2020 | Murdeshwar et al. | |
| 2022/0110680 | A1 | 4/2022 | Walish et al. | |

FOREIGN PATENT DOCUMENTS

| | | |
|---|---|---|
| EP | 3981347 A2 | 4/2022 |
| EP | 3981347 | 7/2025 |

OTHER PUBLICATIONS

"U.S. Appl. No. 17/493,437, Notice of Allowance mailed Jan. 31, 2024", 9 pgs.
"U.S. Appl. No. 17/493,437, Response filed Dec. 18, 2023 to Non Final Office Action mailed Oct. 5, 2023", 9 pgs.
"U.S. Appl. No. 17/493,437, Response filed Sep. 15, 2023 to Restriction Requirement mailed Jul. 24, 2023", 5 pgs.
"U.S. Appl. No. 17/493,437, Restriction Requirement mailed Jul. 24, 2023", 7 pgs.
"European Application Serial No. 21201768.5, Extended European Search Report mailed May 20, 2022", 13 pgs.
"European Application Serial No. 21201768.5, Partial European Search Report mailed Feb. 25, 2022", 14 pgs.
"European Application Serial No. 21201768.5, Response filed Dec. 22, 2022 to Extended European Search Report mailed May 20, 2022", 14 pgs.
"Chinese Application Serial No. 202111172280.0, Office Action mailed Mar. 6, 2025", W/English Translation, 29 pgs.
"Chinese Application Serial No. 202111172280.0, Response filed Jul. 4, 2025 to Office Action mailed Mar. 6, 2025", W English Claims, 16 pgs.
"Chinese Application Serial No. 202111172280.0, Office Action mailed Aug. 18, 2025", W English Translation, 13 pgs.
"European Application Serial No. 25188984.6, Invitation to remedy deficiencies mailed Aug. 21, 2025", 1 pgs.
"European Application Serial No. 25188984.6, Response filed Oct. 14, 2025 to Invitation to remedy deficiencies mailed Aug. 21, 2025", w English Claims, 3 pgs.
"Chinese Application Serial No. 202111172280.0, Response filed Oct. 16, 2025 to Office Action mailed Aug. 18, 2025", w English Claims, 10 pgs.
"Chinese Application Serial No. 202512002960.2, Office Action mailed Dec. 29, 2025", w Machine English translation, 3 pg.
"European Application Serial No. 25188984.6, Extended European Search Report mailed Mar. 5, 2026", 7 pgs.

* cited by examiner

UTERINE MANIPULATOR WITH NEUTRAL RETURN ELECTRODE

CROSS-REFERENCE TO RELATED APPLICATIONS

This application is a Divisional of U.S. patent application Ser. No. 17/493,437, filed Oct. 4, 2021, now U.S. Pat. No. 11,998,267, which claims the benefit of priority to U.S. Provisional Patent Application Ser. No. 63/089,147, filed Oct. 8, 2020, the contents of which are incorporated by reference herein in their entireties.

TECHNICAL FIELD

This document pertains generally, but not by way of limitation, to surgical devices that can be used for various surgical procedures. More specifically, but not by way of limitation, the present application relates to a surgical device that may be used to treat the reproductive system of a female patient.

BACKGROUND

Many surgical procedures involve the treatment or removal of subdermal target tissue, e.g., diseased, or unwanted tissue or growths, located inside of a patient. As such, these procedures require access to and visibility of the internal anatomy of the patient.

The anatomy of the female reproductive system includes, among other things, ovaries, fallopian tubes, a uterus, a cervix and a vagina. As a result of certain gynecological conditions, such as cancers or severe pain and heavy bleeding, it sometimes becomes necessary to treat a patient's uterus. One option for treating the uterus includes surgically removing the uterus via a hysterectomy procedure.

One hysterectomy procedure is known as a total hysterectomy and involves the complete removal of a patient's uterus and cervix. Initially, hysterectomy procedures were performed via an incision in a patient's abdomen. With advancement in surgical tools and procedures, hysterectomy procedures have evolved to include vaginal and laparoscopic techniques. Today, hysterectomy procedures involve one of four primary approaches: total abdominal hysterectomy (TAH), total vaginal hysterectomy (TVH), total laparoscopic hysterectomy (TLH), and laparoscopic supracervical hysterectomy (LSH).

Medical literature has shown that the TLH and LSH can be useful over the conventional TAH and TVH approaches. The TLH and LSH approaches can be desirable because of several potential benefits, including, for example, less post-operative pain, shorter hospital stays, and faster recovery times. It may be beneficial if more hysterectomies performed each year were performed via the TLH or LSH approach. Often, the reasons for performing a hysterectomy without using a TLH or LSH approach include the limitations of laparoscopic surgery in general.

Limitations with performing hysterectomies, and laparoscopic hysterectomies in particular can include limited visibility which can make it difficult to determine if a surgical tool such as a colpotomy cup is located properly, for example, seated against the uterus adjacent the cervix. A colpotomy cup can be used in a cauterization/cutting procedure known as a colpotomy, used to excise the uterus. These challenges can also be present in non-laparoscopic hysterectomies, other uterine treatments and other surgeries as well.

A colpotomy is a procedure by which an incision is made in the vagina, to perform a hysterectomy, to gain access to visualize other pelvic structures, or to perform a surgery on the fallopian tubes or ovaries. To perform a colpotomy, a surgeon guides a medical instrument including an end effector (e.g., end effector assembly) located at a distal end, through the vaginal opening into the vagina of the patient and positions a cutting guide (e.g. a colpotomy cup) of the end effector proximate a surgical site proximate a cervix. The distal end of the end effector can also include a uterine manipulator to shift the uterus around to gain visibility or access to various tissues during a procedure. The cutting guide can be used to guide a cutting device for performing an incision through the vagina proximate to and around the cervix. Performing a colpotomy can be a difficult procedure for a surgeon because other tissues, such as the bowel (e.g., rectum, colon) and bladder are in close proximity to the colpotomy incision site in the vaginal wall. Accordingly, there is a need for improved instruments, systems and methods for performing surgeries, including, but not limited to, surgeries that require a colpotomy procedure.

Some surgeries, including hysterectomies, can be performed via electrosurgery. Electrosurgery can include the passage of electrical current through a target tissue to create a desired tissue effect. Electrosurgical tissue effects can include cutting, coagulation, desiccation, fulguration and ablation. The target tissue acting as a resistor in an electrical circuit is heated by its conduction of the electrical current. There are two main types of electrosurgery, monopolar electrosurgery and bipolar electrosurgery. In monopolar electrosurgery, radiofrequency (RF) current is passed from an electrosurgical generator through an active electrode into targeted tissue where the incision is to be performed. This current then travels through the patient, and is received by a return electrode (e.g., neutral return electrode) and back to the electrosurgical generator. Traditional return electrodes include return electrode mats or pads that are placed in contact with a patient's skin. Return electrode mats are intended to minimize any effect on the tissue at the return electrode.

In bipolar surgery, electrodes are arranged in pairs on the surgical instrument, and do not require a separate return electrode, such as a return electrode mat to be in contact with the patient. The intended flow of current between the pair of bipolar electrodes ("+/−" to "−/+") are usually close together and use relatively low voltage. Thus, bipolar systems usually have a shorter distance between the tissue to be excised and the return electrode.

Limitations with monopolar electrosurgery include the current traveling through the patient between the active electrode and the return electrode. The distance between a target tissue at a surgical location, such as the distance between a uterus and the location of a return electrode mat placed under the patient or a pad adhered to the skin of the patient, results in the energy having to travel through the patient from the target tissue, such as the uterus, through the intervening tissue to the skin on a torso or leg, before being received by the return electrode pad where the energy is collected and returned to the electrosurgical generator. Monopolar electrosurgery generally requires a higher voltage than bipolar electrosurgery. Furthermore, if the return electrode is not in good contact with the patient, or if the contact area is not sufficient to disperse the current, heating of tissue can occur. If a surgeon is unable to determine if a return electrode is properly placed and in sufficient contact with the patient, current flow at the return electrode can exceed a target range.

Accordingly, there is a need for improved instruments, systems and methods for electrosurgery to minimize current flow through, and effects on, the tissue that is not the target tissue, to monitor if a return electrode is in sufficient contact with the patient.

OVERVIEW

The present inventors have recognized, among other things, that problems to be solved in performing tissue resection procedures such as a colpotomy include a desire to better focus and control electrical energy applied to a target tissue while minimizing damage to non-target tissue. Additionally, the inventors have recognized it would be useful if a surgeon could determine if a medical device, such as a colpotomy cup or other uterine device is in a desired position, in a treatment position, in a surgical position, is fully inserted or is properly seated in-situ. The present subject matter can provide solutions to these problems and other problems and is not limited to colpotomy and other uterine procedures.

The present disclosure can be used with systems and methods to vaginally deliver a neutral return electrode for electrosurgery and other tissue treatments that include applying an electrical signal to a tissue. In some examples, the neutral return electrode can be used to position a guide, or the guide can be used to position the neutral return electrode. In some examples, the neutral return electrode can be used to locate a guide such as a tissue resection device relative to physical anatomy, such as locating an end effector for performing a colpotomy relative to at least one of: a cervix, cervical lumen, vaginal fornix. cervical-vaginal junction or other anatomical location, or for anchoring the end effector relative to the anatomy.

In an example, a uterine manipulator includes an elongate shaft including a distal portion configured to be inserted into a uterus through a lumen of a cervix, and a split return electrode coupled to the elongate shaft. The split return electrode can be configured to be electrically coupled to an electrosurgical generator.

In an example, a method of determining an in-situ position of a vaginally-insertable uterine device includes: issuing a drive signal to be received by a split return electrode located on the uterine device; receiving at least a portion of the issued drive signal from the split return electrode; monitoring an electrical property of the split return electrode based on the issued drive signal and the received at least a portion of the issued drive signal to determine if a threshold has been traversed; and based at least in part on the threshold being traversed, permitting issuance of a second signal to an active electrode.

In an example, a tissue resection system includes a uterine manipulator including an elongate shaft having a distal portion configured to be inserted into a uterus through a lumen of a cervix, a split return electrode coupled to the elongate shaft, the split return electrode having a first electrode and a second electrode, the split return electrode configured to be electrically coupled to an electrosurgical generator. The tissue resection system can further include a colpotomy cup coupled to the elongate shaft, the colpotomy cup configured to be positioned in-situ around a cervix, wherein a distal portion of the colpotomy cup is configured to delineate a target tissue to be treated, and a cutting device including an active electrode to treat the target tissue, the cutting device configured to be electrically connected to an output of an electrosurgical generator.

In an example, an end effector of a tissue treatment device includes a uterine manipulator, a colpotomy cup coupled to the uterine manipulator, and a protrusion including a return electrode member configured to be electrically connected to an electrosurgical generator. The uterine manipulator includes an elongate shaft having a distal end portion, wherein the distal end portion is configured to be inserted into a lumen of a cervix. The colpotomy cup includes a cut guide having an outer wall portion and a base portion supporting the outer wall portion, the outer wall portion is configured to surround at least a portion of the cervix, the outer wall portion extending from a first proximal end portion to a first distal end portion along a longitudinal path. The protrusion extends distally away from the base portion and is laterally spaced away from the outer wall portion. The protrusion extends along the longitudinal path such that the protrusion is configured to be inserted into a lumen of the cervix.

In an example, an end effector of a tissue treatment device includes a uterine manipulator including an elongate shaft extending from a proximal end portion to a distal end portion, wherein the distal end portion is configured to be inserted into a lumen of a cervix. A colpotomy cup is coupled to the elongate shaft. A return electrode member is coupled to the colpotomy cup, the return electrode member configured to be electrically connected to an electrosurgical generator. In addition, the return electrode member is actuatable to change from a first state to a second state, wherein in the first state, the return electrode member is configured to be inserted into the lumen of the cervix and wherein in the second state, the return electrode member is configured to inhibit removal of the inserted return electrode member proximally relative to the lumen of the cervix.

In an example, an end effector of a tissue treatment device including an elongate shaft extending from a proximal end portion to a distal end portion. The proximal end portion is manipulatable by a user or a machine to deliver the distal end portion to a treatment site, and the distal end portion is configured to be inserted into a lumen of a cervix. A return electrode is coupled to the distal end portion, and the return electrode is configured to be electrically coupled to an electrosurgical generator. The return electrode is configured to inhibit proximal movement of the elongate shaft relative to the lumen of the cervix when the return electrode is positioned in the lumen of the cervix.

In an example, a tissue resection system includes a cutting device including an active electrode configured to receive a signal from surgical generator and a cut guide configured to be inserted into a patient. The cut guide extending from a proximal end to an opening at a distal end. The distal end includes a perimeter return electrode around the opening, and the perimeter return electrode is configured to be electrically connected to an electrosurgical generator.

This overview is intended to provide an overview of subject matter of the present patent application. It is not intended to provide an exclusive or exhaustive explanation of the invention. The detailed description is included to provide further information about the present patent application.

Figure 1:
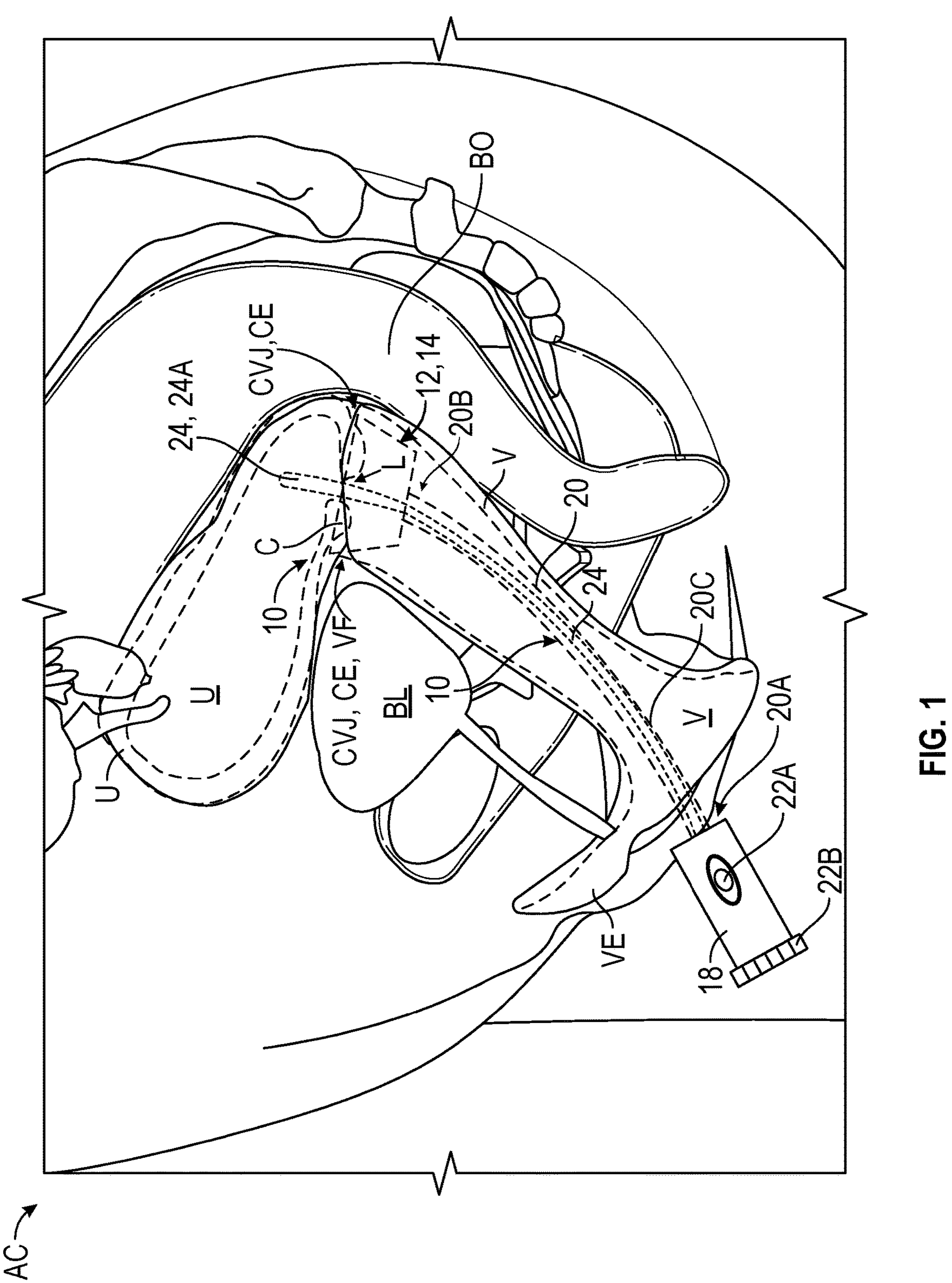
FIG. 1 is a schematic illustration of a medial view of female anatomy in an abdominal cavity including a portion of a medical instrument inserted into a vagina, in accordance with at least one example.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure provides systems and methods for performing a colpotomy procedure as part of a hysterectomy or other surgery. The present application is described with reference to performing female pelvic procedures, such as a colpotomy. However, the systems and methods of the present disclosure can be used with other procedures of the female reproductive system are not limited to colpotomy procedures. In particular, the systems and methods can be used in other procedures, such as those that benefit from: focusing energy into a target tissue to be dissected or otherwise treated while minimizing energy transfer to non-target tissue. Further, the examples described in the present disclosure may also be used in the treatment, dissection and/or removal of other tissue or organs in both males and females, including but not limited to procedures of the colon, or esophagus. For the purposes of this disclosure, “proximal” refers to the end of the device closer to the device operator during use, and “distal” refers to the device end further from the device operator during use (e.g., See FIG. 9).

FIG. 1 is a schematic illustration of a medial view of female anatomy in an abdominal cavity AC including a portion of a medical instrument 10 inserted into the vagina V of a patient. Normal female pelvic anatomy includes, among other things, a uterus U, a cervix C, vagina V, bladder BL and bowel BO. One of the challenges with performing a colpotomy is the proximity of the cervical-vaginal junction CVJ (e.g., vaginal fornix or fornices VF) to other organs.

Figure 2:
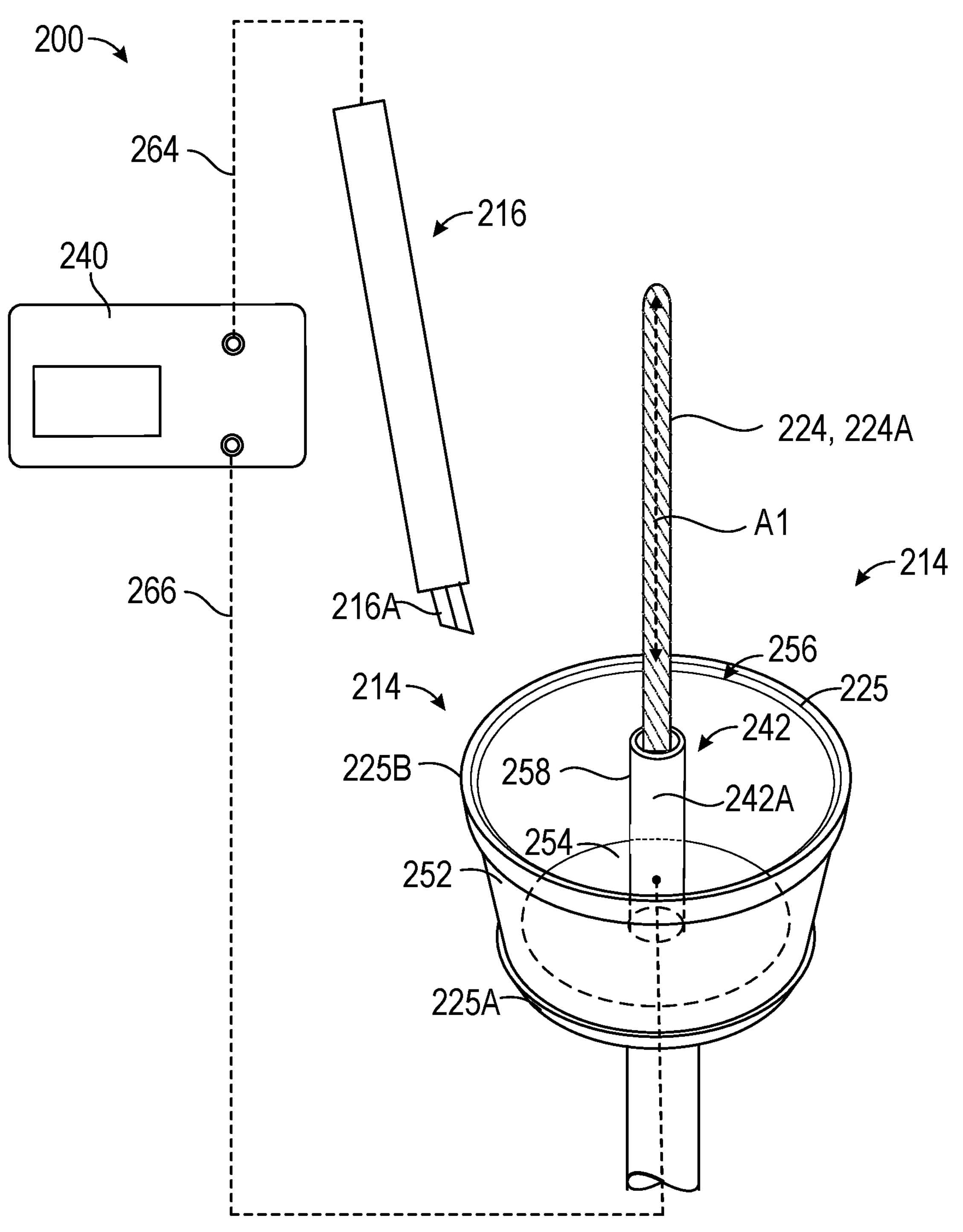
FIG. 2 is a schematic illustration of a surgical system including an electrosurgical generator assembly, and an isometric view of a portion of an end effector having a return electrode member, and a monopolar cutting device, in accordance with at least one example.

To perform a colpotomy, a surgeon or other operator inserts a distal portion 12 of the medical instrument 10 including an end effector 14 into a vulvar end VE of a patient’s vagina V, guiding the end effector 14 through the passageway of the vagina V, and seating the end effector 14 proximate a cervical end CE of the vagina V adjacent a vaginal fornix VF. The end effector 14, as will be discussed further below, can be used as a cut guide to perform a resection during a hysterectomy. In some examples, and as shown in FIG. 2, the end effector 14 can provide a surgeon a cut guide to be used in conjunction with a separate monopolar electrosurgical cutting device. With the end effector 14 in place, the surgeon can perform the cut. The example of an end effector 14 for performing a colpotomy is provided as an illustrative example. In some examples, an end effector can be configured to provide a guide for seating the medical instrument 10 against a locating tissue without providing a cut guide.

Figure 3:
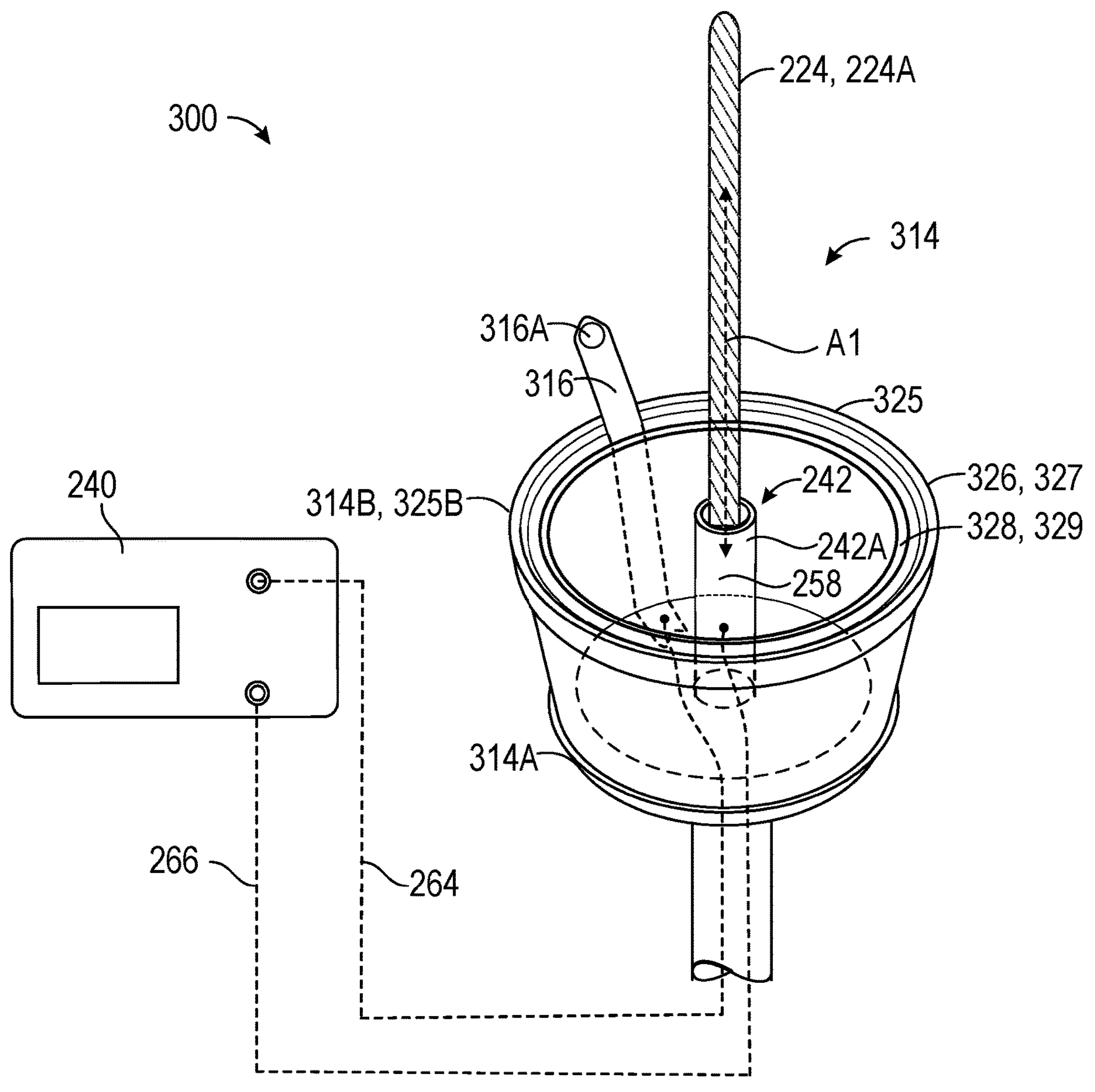
FIG. 3 is a schematic illustration of a second surgical system including an electrosurgical generator assembly, and an isometric view of a portion of a second end effector having the return electrode member of FIG. 2 and an integral cutting device, in accordance with at least one example.
Figure 4:
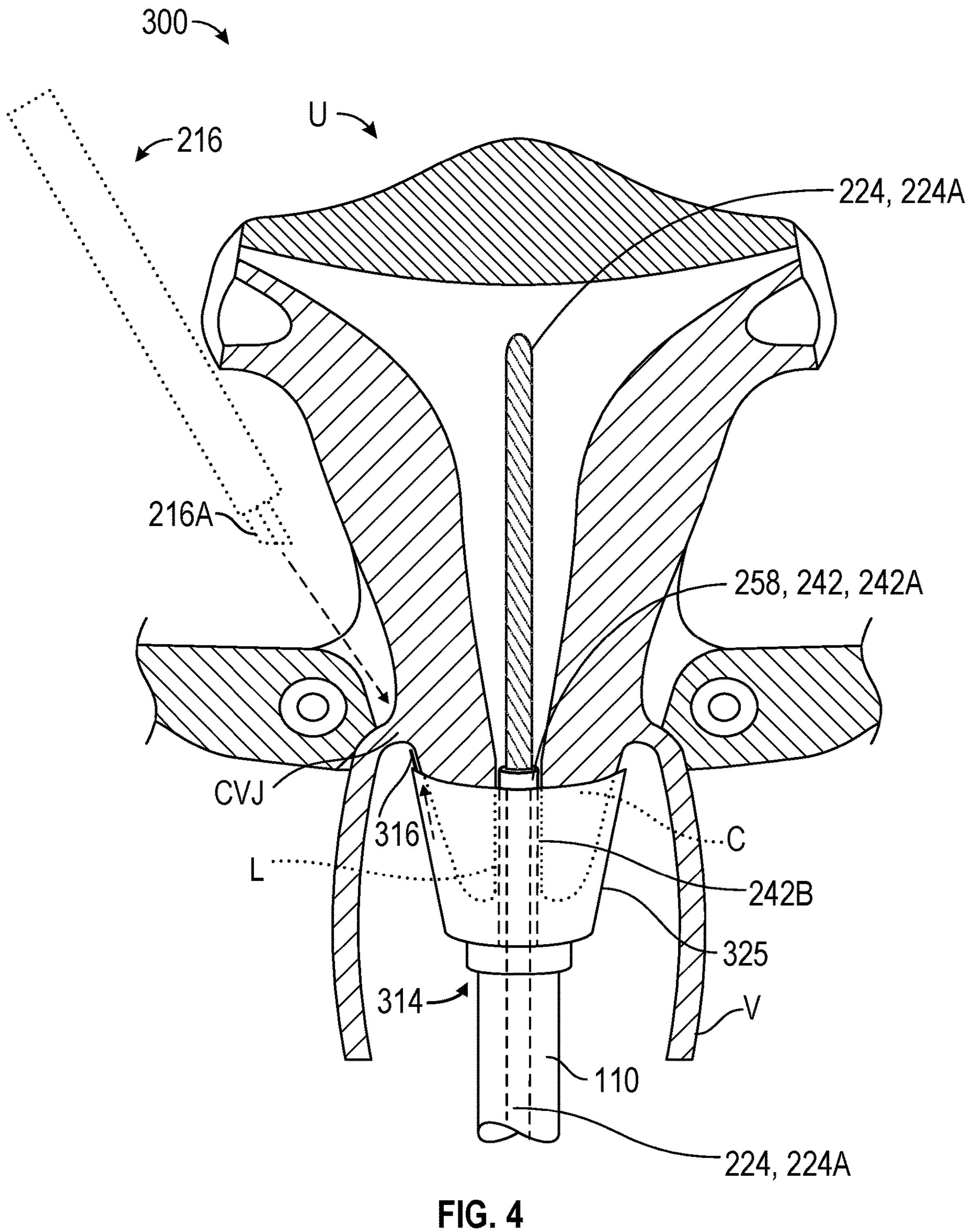
FIG. 4 is a cross-sectional illustration of female anatomy with the end effector of FIG. 3 with the return electrode member inserted into a cervix, in accordance with at least one example.

The surgeon can perform the cut with a variety of different cutting devices. For example, as shown in FIG. 2, the surgeon can move a separate monopolar cutting device 216 along a distal end of an end effector 214 to cut the vaginal tissue around the cervix C. In other examples, and as shown in FIG. 3, an end effector 314 can include an integral electrosurgical cutting device (e.g., 316) that can be actuated to rotate about a distal end of the end effector 314. The integral electrosurgical cutting device 316 can perform the cut from the vaginal side of the cervical-vaginal junction CVJ (FIG. 4). In some procedures, the cutting device 216 or 316 can be used to make a 360 degree cut in the vaginal wall VW to separate the cervix C and uterus U from the vagina V thereby facilitating resection of the uterus U and cervix C from the patient (FIG. 1).

Returning to FIG. 1, the medical instrument 10 can include a handle portion 18, a delivery member 20 and the end effector 14. The handle portion 18 and delivery member 20 can aid a device operator in delivering the end effector 14 to the cervical end CE of the vagina V. The handle portion 18 can be located at a proximal end portion 20A of the delivery member 20 and the end effector 14 can be located at a distal end portion 20B of the delivery member 20.

The delivery member 20 can include a body extending from the proximal portion to the distal portion and can include a lumen 20C extending therethrough. In the example, the handle portion 18 or the delivery member 20 can include one or more operator controls 22A, 22B to actuate the end effector 14, such as to operate the uterine manipulator 24 or the cutting device 16. In some examples, the handle portion 18 and the one or more operator controls 22A, 22B can be omitted, modified or located elsewhere, such as to permit the use and operation of the medical instrument 10 in robotic surgery, or in a procedure actuated remotely or partially remotely. Any number of operator controls 22A, 22B including actuators, may be provided. The handle portion 18 is shown to illustrate one possible example.

A movable uterine manipulator 24 of end effector 14 can include an elongate shaft 24A that can be inserted into an opening of the cervix C and through a lumen L of the cervix C into the uterus U. The uterine manipulator 24 can be configured to allow a surgeon to move the uterus U around during surgery to provide access to locations to be resected. Features of the uterine manipulators described herein can be used together with or separately from the features described herein with respect to guides, cut guides and colpotomy cups of the end effector.

FIG. 2 is a schematic illustration of a surgical system 200 including an electrosurgical generator 40 (hereinafter, generator 40), and an isometric view of a portion of an end effector 214 and a monopolar cutting device 216. FIG. 3 is similar to FIG. 2, except that FIG. 3 includes an example of an end effector 314 having an integral cutting device 316.

Electrosurgery involves application of high radio frequency electrical current to a surgical site to cut, ablate, coagulate or seal tissue. In conventional monopolar surgical systems, an active electrode is typically part of a surgical instrument that is held by a surgeon and applied to tissue to be treated. The active electrode is configured to deliver a therapeutic energy to the tissue. A patient return electrode is placed remotely from the active electrode to safely disperse the current delivered by the active electrode and to carry the current back to the surgical generator.

In conventional monopolar surgical systems used to perform colpotomy procedures, the active electrode resides on an electrosurgical cutting device that can be inserted, for example, laparoscopically into the body or into an open surgical site to access a first surface of a target tissue, while the return electrode resides on a pad that is adhered to a skin of the patient, such as the back, torso or leg. Thus, energy delivered from an electrosurgical cutting device relies on the energy having to travel from the active electrode to the target tissue (e.g., vaginal fornices, proximate the cervix), resect the target tissue from the first surface through to a second surface of the tissue, and then through the patient's body tissue until it reaches a return electrode pad that is adhered to the skin, usually on a leg or torso.

In contrast to conventional monopolar surgical systems, as shown in the illustrative surgical systems 200, 300 of FIGS. 2 and 3, a return electrode 242A can be located on a return electrode member 242 that is located closer to the treatment location (e.g., the cervical-vaginal junction CVJ shown in FIGS. 1, 4).

As shown in FIG. 2, the end effector 214 can include a colpotomy cup 225 that can include an outer wall portion 252 configured to surround at least a portion of the cervix C, and a base portion 254 supporting the outer wall portion 252. The base portion 254 configured to be located proximal of the opening to the cervix C. The outer wall portion 252 can extend from a proximal end portion 225A to a distal end portion 225B along a longitudinal path A1. The distal end portion can include an opening to receive the cervix C. Together, the outer wall portion 252 and the base portion 254 can form a capture portion and define a cavity 256 to receive the cervix C. The distal end portion 225B of the colpotomy cup 225 can be configured to delineate the target tissue to be treated by the cutting device and to provide a cutting guide for a surgeon to trace with the monopolar electrosurgical device 216.

A protrusion 258 can extend distally away from the base portion 254 into the cavity 256 and can include a return electrode member 242. The protrusion 258 can be laterally spaced away from the outer wall portion 252. The protrusion 258, including the return electrode member 242, can extend along the longitudinal path (such as, but not limited to longitudinal axis A1). The protrusion 258 can be generally centrally located within the colpotomy cup 225 such that the return electrode member 242 can be inserted into the cervical opening C and can remain in contact with the lumen L of the cervix C while an outer wall portion 252 of the colpotomy cup 225 is located around the cervix C (see positioning in the example of FIG. 4). The return electrode 242A can be configured to be electrically connected to the electrosurgical generator 240 to receive and return the therapeutic energy delivered to the active electrode 216A via active lead 264 back to the electrosurgical generator 240 via lead 266.

The systems of FIGS. 2 and 3 thus beneficially locates a return electrode closer to the resection location than conventional monopolar electrosurgical systems which rely on a return electrode pad adhered to a patient's skin. In this arrangement, the therapeutic energy delivered by the active electrode 216 (or 316) does not need to travel as a large a distance through the patient's body tissue before being collected by the return electrode member 242 and delivered back to the electrosurgical generator 240.

The end effectors of FIGS. 2 and 3 can also include a movable uterine manipulator 224. The uterine manipulator 224 can be configured to allow a surgeon to move the uterus U around during surgery to provide access to locations to be resected, such as near the cervical-vaginal junction CJV (FIGS. 1, 4). The uterine manipulator 224 can include an elongate shaft 224A that can be inserted into an opening of the cervix C and through a lumen L of the cervix C into the uterus U (FIGS. 1, 4). In some examples, and as shown, the elongate shaft 224A can extend through the protrusion 258. In other words, the elongate shaft 224A can extend through the return electrode member 242. The uterine manipulator 224 can be coupled to the colpotomy cup 225 and can be actuated by the controls on the handle (FIG. 1). In some examples, the uterine manipulator 224 can be fixedly coupled to the colpotomy cup 225. In other examples the uterine manipulator 224 may be slidably or rotatably coupled to the colpotomy cup 225.

The surgical system 300 of FIG. 3 is similar to the surgical system of FIG. 2. However, while FIG. 2 relies on a separate monopolar electrosurgical device 216 to provide the current to treat the tissue (e.g., a separate cutting device), FIG. 3 includes an integral electrosurgical cutting device 316 having the active electrode 316A. Like numerals can represent like elements, therefore not all elements may be described in further detail.

The end effector 314 can extend along a longitudinal axis A1 from a proximal end 314A to a distal end 314B. In some examples, an axis is not required, and the longitudinal axis A1 can instead be described as a general longitudinal path or a longitudinal direction. An axis is shown for the purposes of describing one illustrative example. The end effector 314 can include a first cut guide 326, a second cut guide 328, and a cutting device 316 located between the first cut guide 326 and the second cut guide 328. The end effector 314 can also include a cutting device actuator configured to deploy the cutting device 316 distally. The distal end portion 325B of the colpotomy cup 325 can provide a cutting guide for the integral electrosurgical cutting device 316. In some examples, only the first cut guide or the second cut guide may be provided.

The cutting device 316 can be rotatably coupled to the colpotomy cup 325 and located between the first cut guide 326 having a first distal peripheral portion 327 and the second cut guide 328 having a second distal peripheral portion 329. The second cut guide 328 can be located around the first cut guide 326. The cutting device 316 can be moveable relative to at least one of the first distal peripheral portion 327 and the second distal peripheral portion 329 to move along a periphery of the colpotomy cup 325 to treat the target tissue. The periphery can be circumferential, oblong, oval, or any other suitable shape to facilitate the desired treatment of the target tissue. The cutting device 316 can be deployed by operator controls (22A, 22B; FIG. 1) including an actuator (e.g., actuating mechanism). The actuator can be any suitable actuator, such as a mechanical or electrical actuator that is configured to actuate movement of the cutting device 316 to cause at least portion of the cutting device 316 to protrude beyond the distal end portion 325B of the colpotomy cup 325.

The actuator can be located in any suitable location on the medical instrument (e.g., 10, FIG. 1) to facilitate actuation of the cutting device 316, such as located at one or more of: the end effector 314 (FIG. 3), the delivery member 20 and the handle portion 18 (FIG. 1).

For example, movement between the deployed and retracted positions may be accomplished via the first user control 22A (FIG. 1) including a first actuating mechanism such as a slide actuator that can be operably coupled to the cutting device 316. The first actuating mechanism can be any actuating mechanism known to one skilled in the art for deploying a cutting device.

Rotational movement can be accomplished via a second user control 22B (FIG. 1) including a second actuating mechanism, such as a rotational actuator. In one example, the second actuation mechanism can facilitate rotation of a shaft within the delivery member 20 while the shaft is coupled to the cutting device 316. The second actuating mechanism can be any actuating mechanism known to one skilled in the art for controlling rotation of the cutting device 316.

In conventional monopolar surgical systems, an active electrode resides on a surgical instrument that can be inserted, for example, laparoscopically into the body, while the return electrode resides on a pad that is adhered to a skin of the patient. In contrast, the surgical system 300 of FIG. 3 can include an active electrode that resides on the end effector and a return electrode that also resides on the end effector. The surgical system 300 of FIG. 3 is arranged as a monopolar surgical system, however, because of the decreased distance between the active electrode 316A and the return electrode member 242 compared to other monopolar systems, the surgical system 300 of FIG. 3 can act more like a hybrid between a monopolar and a bipolar system. In particular, because both the active electrode 316A and the return electrode member 242 can be located close together, and even on the same end effector 314, instead of being located on two separate devices spaced further apart, the surgical system 300 can take on this pseudo-bipolar aspect. Further, although the surgical system 300 is depicted as a monopolar system, in some examples, the end effector 314 could be configured to be electrically connected to a bipolar electrosurgical generator instead of the monopolar electrosurgical generator 340.

FIG. 4 is a cross-sectional illustration of female anatomy with the end effector of FIG. 3 inserted into a cervix. FIG. 4 shows the end effector having the integral cutting device of FIG. 3. In addition, FIG. 4 also illustrates the alternate cutting device 216 (a separate monopolar electrosurgical device) of FIG. 2 in dotted line. Like numerals can represent like elements, therefore not all elements may be described in further detail.

As shown in FIG. 4, when the end effector 314 is vaginally inserted with the colpotomy cup 325 located proximate a cervix C or positioned in-situ around the cervix C, an outer surface 242B of the return electrode member 242 is configured to be located in contact with the lumen L of the cervix C. In this position, the distance between the application of therapeutic energy to the tissue at the cervical-vaginal junction CVJ only needs to travel to the return electrode member 242 that is inserted into the cervical lumen L, instead of as in conventional colpotomy procedures where the therapeutic energy has to travel all the way to the skin before being returned to the electrosurgical generator.

In addition, the location of the return electrode member 242 within the cervical lumen L can be a beneficial location for collecting the therapeutic energy for other steps in a hysterectomy procedure besides a colpotomy. The location of the return electrode member 242 in the lumen L of the cervix C, can also be beneficially used in other procedures, including procedures of the abdominal cavity, such as, but not limited to, the rectum, colon or bladder, because such organs are located in close proximity to the cervix C or uterus U.

Figure 5:
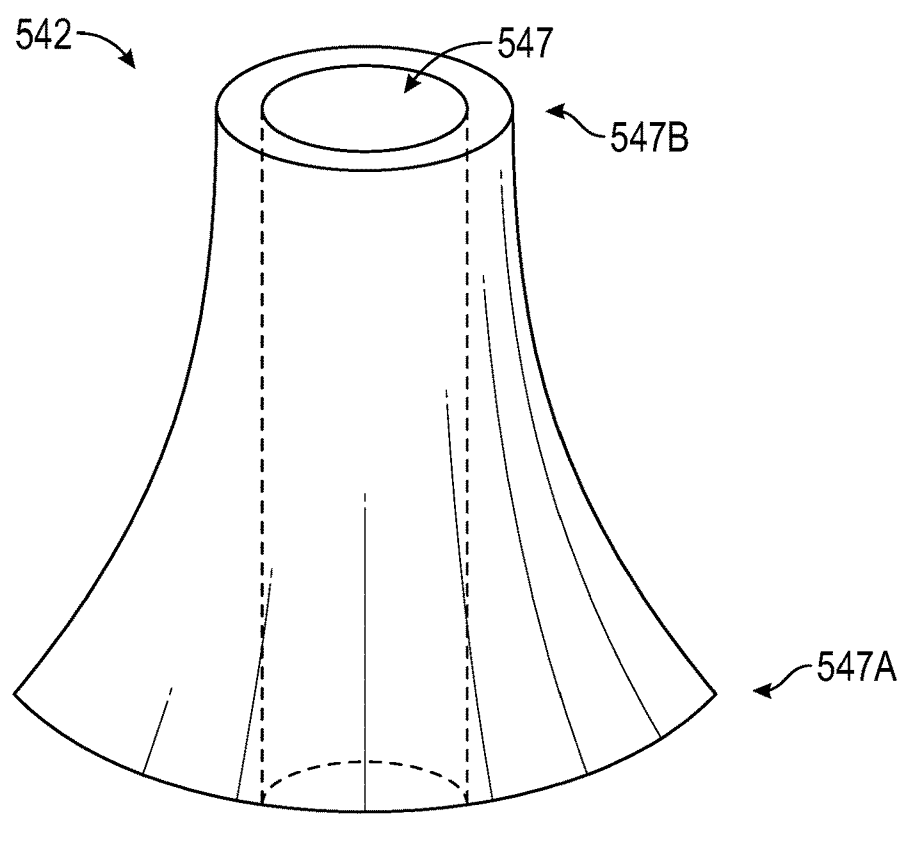
FIG. 5 is a schematic illustration of an isometric view of a second return electrode member that can be used with the end effectors described herein, in accordance with at least one example.

FIGS. 5, 6, 7A, 7B and 8 show various configurations of return electrode members that can be used with the return electrode member 242 described in FIGS. 2-4. For example, FIG. 5 is a schematic illustration of an isometric view of a second example of a return electrode member 542 that can be used with the end effectors described herein. The return electrode member 542 can form an anchor that is configured to inhibit egress of the distal portion of the end effector (e.g., 314, uterine manipulator 224, FIG. 3) proximally through the lumen L of the cervix C when the end effector is positioned in-situ. The return electrode member 542 can have an aperture 547 extending from a proximal end portion 547A to a distal end portion 547B to receive the uterine manipulator (224, FIG. 3) therethrough. In other examples, the return electrode member 542, as well as the return electrode members described in FIGS. 6, 7A, 7B and 8, can be located on a uterine manipulator (e.g., 224) or be formed as part of a uterine manipulator, with or without a colptomy cup (e.g., 225).

As shown in FIG. 5, the return electrode member 542 can include a shape that inhibits egress such as a tapered cylinder or cone. The shape of the tapered cylinder can be configured to anchor the return electrode member relative to the lumen of the cervix. Other tapered shapes can be provided, such as but not limited to, pyramids, spheres, cuboid, fluted and irregular shapes.

Figure 6:
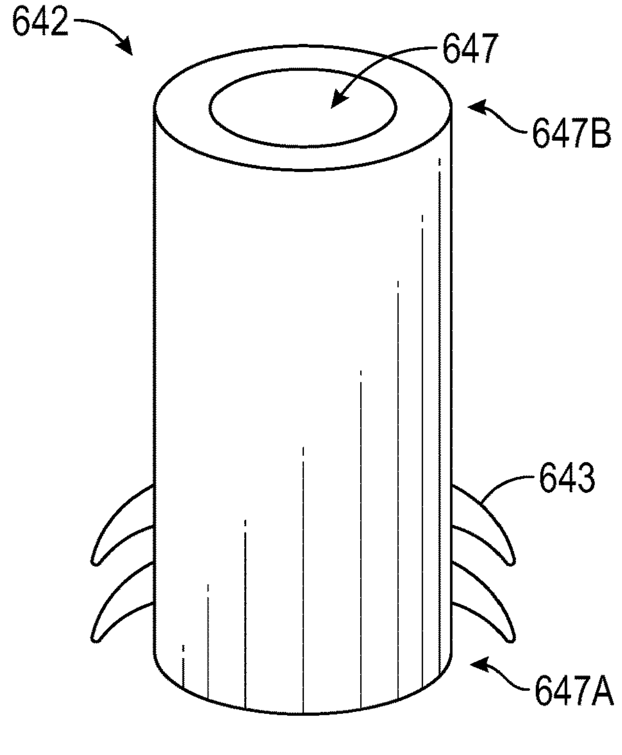
FIG. 6 is a schematic illustration of an isometric view of a third return electrode member that can be used with the end effectors described herein, in accordance with at least one example.

FIG. 6 is a schematic illustration of an isometric view of a third example of a return electrode member 642 in the form of an anchor (e.g., electrode anchor) that can be used with the end effectors described herein. As shown in FIG. 6, the return electrode member 642 can include barbs 643. The barbs 643 can be shaped to allow easy insertion but to inhibit (though may not altogether prevent) egress once inserted. The return electrode member 642 can have an aperture 647 extending from a proximal end portion 647A to a distal end portion 647B to receive the uterine manipulator (224, FIG. 3) therethrough.

Figure 7A:
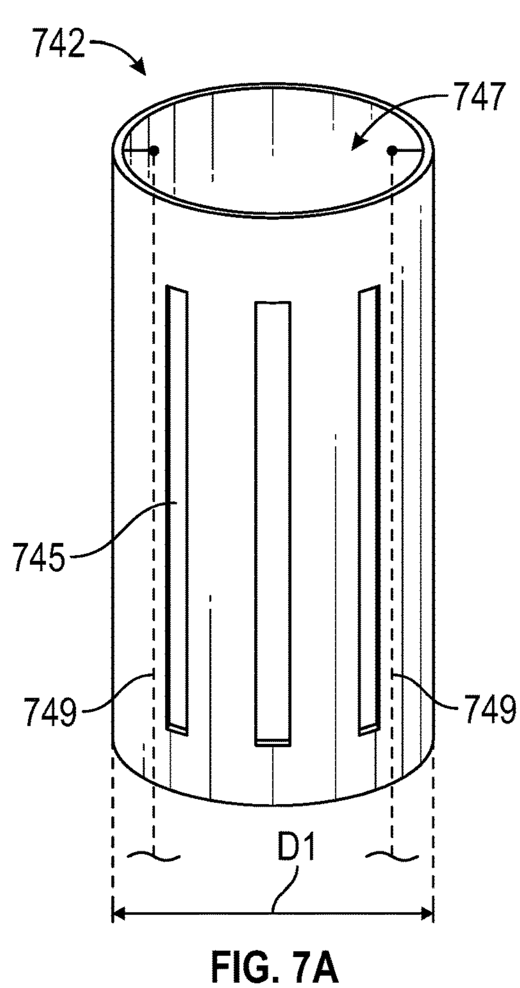
FIG. 7A is a schematic illustration of an isometric view of a fourth return electrode member that can be used with the end effectors described herein, in a first state, in accordance with at least one example.
Figure 7B:
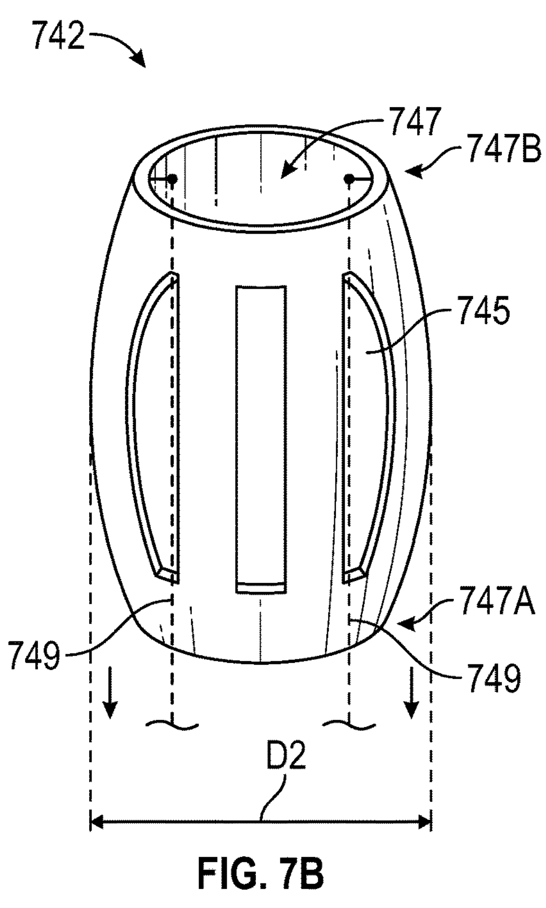
FIG. 7B is a schematic illustration of an isometric view of the fourth return electrode member that can be used with the end effectors described herein, in a second state, in accordance with at least one example.

FIGS. 7A and 7B are schematic illustrations of an isometric view of a fourth example of a return electrode member 742 in the form of an anchor (e.g., electrode anchor) that can be used with the end effectors described herein. FIG. 7A shows the return electrode member 742 in a first state, and FIG. 7B shows the return electrode member 742 in a second state. The return electrode member 742 can include a tube having slots 745 that is deformable to change the return electrode member 742 from a first state to a second state. The change from a first state to a second state can be caused by, for example, mechanical actuation or electrical actuation. In an example, a proximal end portion 747A of the return electrode member 742 can be fixed to the colpotomy cup 325 such as in FIG. 3, while a distal end portion 747B of the return electrode member 742 is movable relative to the colpotomy cut 225. When at least one cable 749 is pulled distally as shown in FIG. 7B, the distal end portion 747B can move proximally, thereby deforming the return electrode member 742. The return electrode member 742 can deform to cause a change in cross-section in a plane normal to the longitudinal axis A1 (FIG. 3), such as to change from a first diameter D1 to a second diameter D2, although the cross-section need not be circular. The return electrode member 742 can have an aperture 747 extending from a proximal end portion 747A to a distal end portion 747B to receive the uterine manipulator (224, FIG. 3) therethrough.

Figure 8:
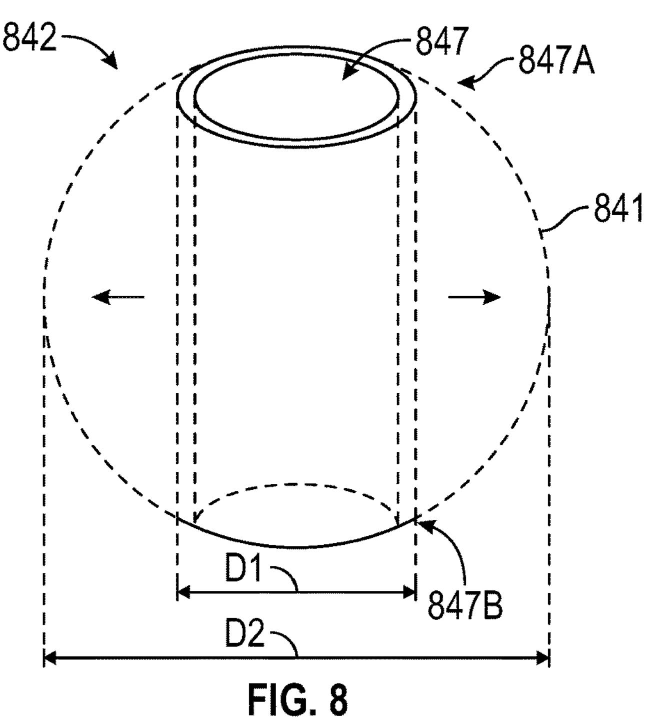
FIG. 8 is a schematic illustration of an isometric view of a fifth return electrode member that can be used with the end effectors described herein, depicting a first state and a second state, in accordance with at least one example.

FIG. 8 is a schematic illustration of an isometric view of a fifth example of a return electrode member 842 in the form of an electrode anchor that can be used with the end effectors described herein. FIG. 8 depicts the return electrode member 842 in both a first state and a second state. The return electrode member 842 can include a balloon 841 that can be expanded, such as by inflation with a fluid that is actuatable by a user or a machine (such as at a control on the handle (FIG. 1)), to change the size and shape of the return electrode member 842. In an example, an inflation fluid can include a gas or a liquid, such as air, carbon dioxide or saline or water. In some examples, to receive and transmit electrical energy, the balloon 841 can include at least one of: a conductive material; a conductive material disposed on the balloon 841; a conductive material impregnated into the balloon 841, or provided as a lattice of conductive material surrounding the balloon 841. The return electrode member 842 can have an aperture 847 extending from a proximal end portion 847A to a distal end portion 847B to receive the uterine manipulator (224, FIG. 3) therethrough.

As shown in FIGS. 7A-7B and FIG. 8, the return electrode member 742, 842 can form an anchor (e.g., electrode anchor) can be actuatable to change from a first state to a second state. In the first state, the return electrode member 742, 842 can be configured to be inserted into the lumen L of the cervix C (FIG. 4). In the second state, the return electrode member 742, 842 can be configured to inhibit removal of the inserted return electrode member 742, 842 proximally relative to the lumen L of the cervix C. In some examples, the return electrode member 742, 842 can have a first size in a first state and a second size in a second state, wherein the second size is greater than the first size. In some examples, the return electrode member 742, 842 can have a first diameter D1 in a first state and a second diameter D2 in a second state. The first diameter D1 can be smaller than the second diameter D2. In some examples, the first state can be described as a collapsed state and the second state can be described as an expanded state. In the collapsed state, the return electrode member 742, 842 may more easily pass through the lumen L of the cervix C than in the expanded state. For example, the return electrode member 742, 842 can have a smaller diameter or other cross section along a plane perpendicular to the longitudinal path A1 (FIG. 4).

Figure 9:
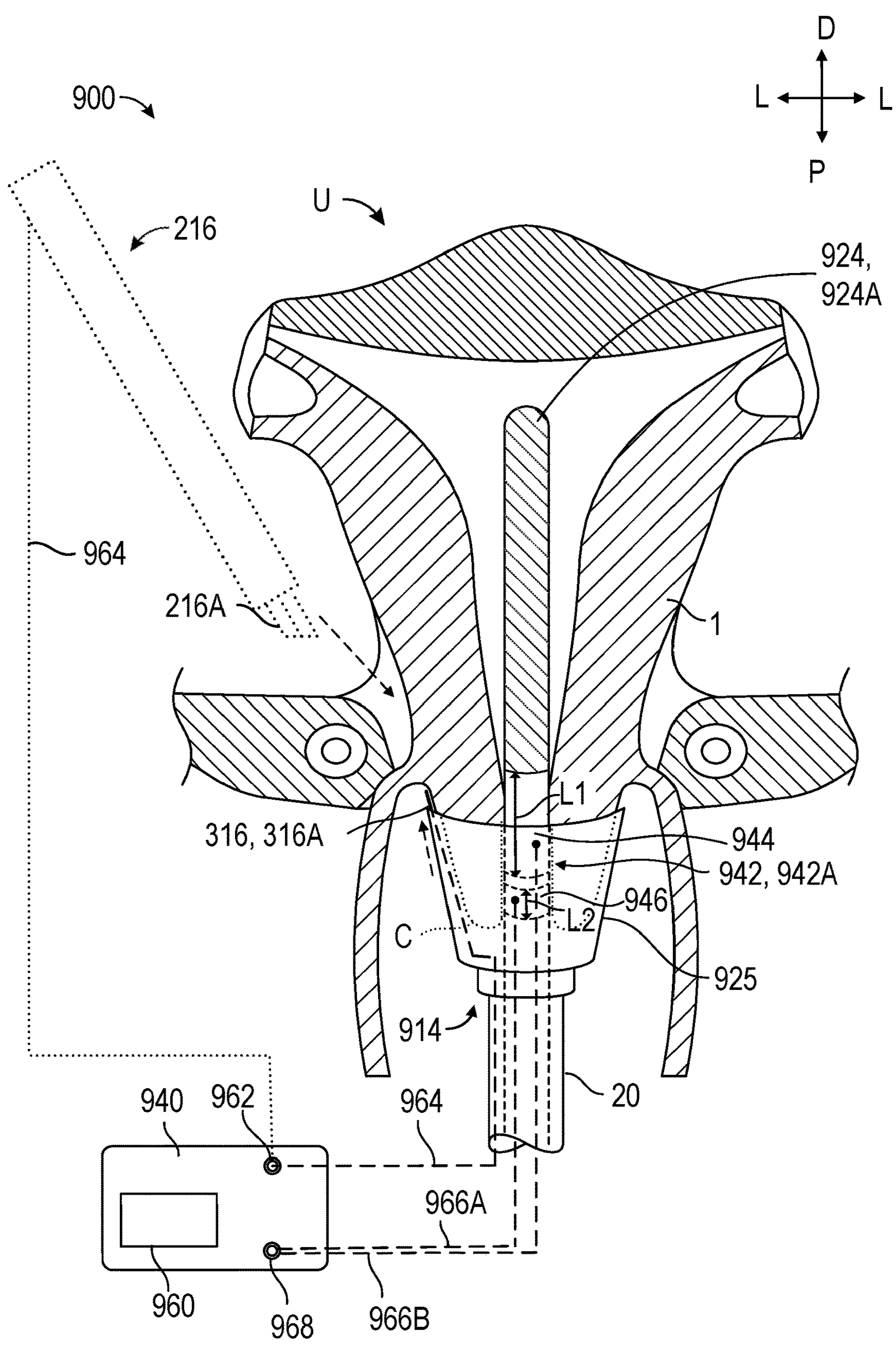
FIG. 9 is a schematic illustration of a surgical system including an electrosurgical generator assembly and including a cross-sectional illustration of female anatomy with third example of an end effector inserted into a cervix, with the end effector electrically connected to the electrosurgical generator, in accordance with at least one example.
Figure 10:
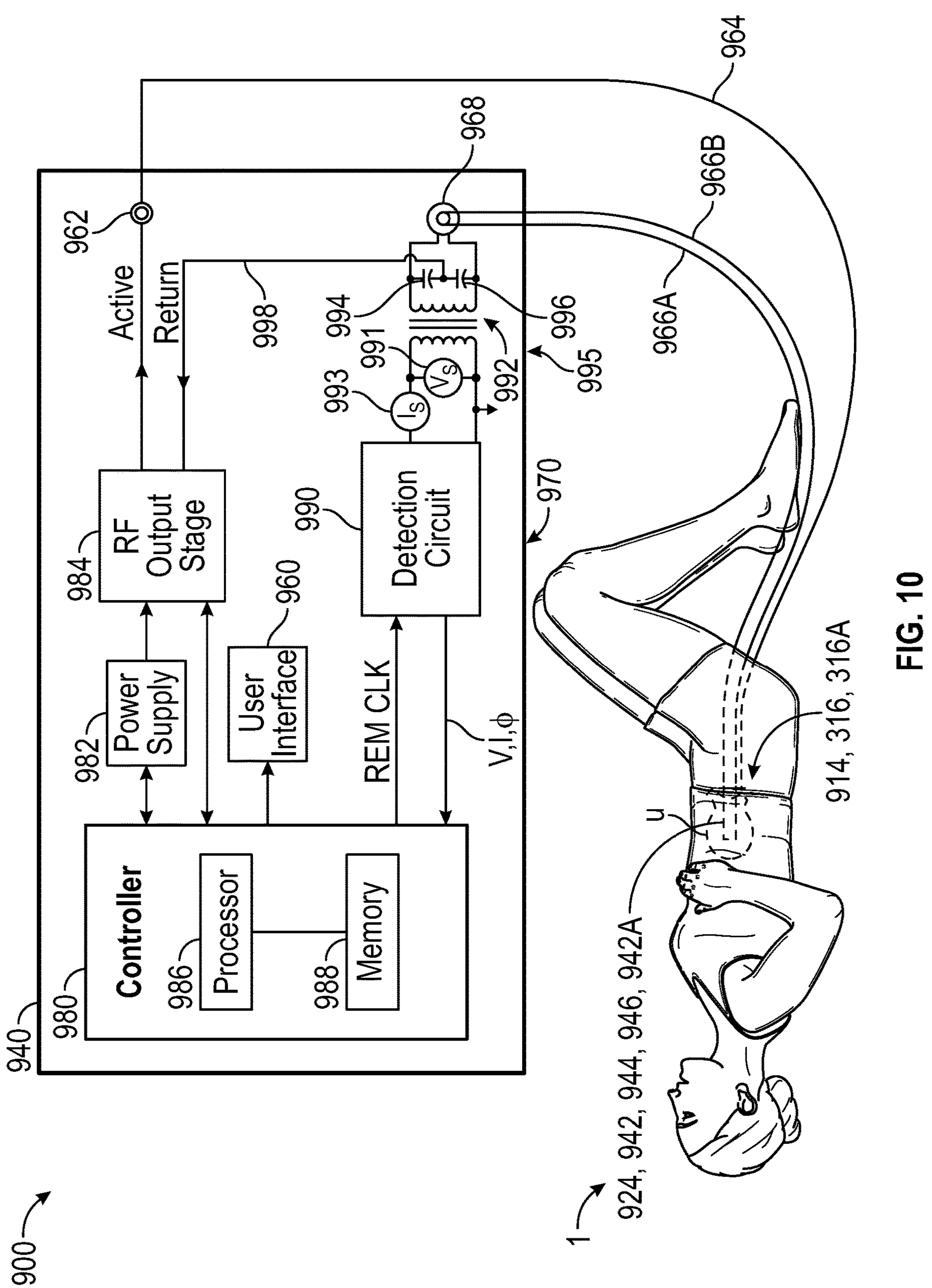
FIG. 10 is a schematic illustration of a surgical system and a patient, in accordance with at least one example.

FIGS. 9 and 10 are described together. FIG. 9 is a schematic illustration of a surgical system 900 including an electrosurgical generator 940 (hereinafter, generator 940) with a cross-sectional illustration of female anatomy having a fourth example of an end effector 914 inserted into a cervix C. Features related to FIG. 9 may also be shown and described in FIG. 10. FIG. 10 is a schematic block diagram of the surgical system 900 of FIG. 9 including the generator 940 and the connection with the patient 1 during use. Like numerals can represent like elements, therefore not all elements may be described in further detail.

A movable uterine manipulator 924 of end effector 914 can include an elongate shaft 924A that can be inserted into an opening of the cervix C and through a lumen L of the cervix C into the uterus U. The uterine manipulator (e.g., 924) can be configured to allow a surgeon to move the uterus U around during surgery to provide access to locations to be resected. The uterine manipulator 924 can include a return electrode member 942 coupled to the elongate shaft 924A.

The return electrode member 942 can include a split return electrode 942A. The split return electrode 942A can provide multiple benefits. Some of the benefits of the split return electrode include returning current to generator 940, being part of a return electrode monitoring (REM) system to monitor if there is sufficient contact of the split return electrode member 942A with tissue, and to determine if the end effector 914 is properly inserted and located. Determining if an end effector 914 is properly inserted in a patient 1 can include providing the end effector 914, including the uterine manipulator 924 having the split return electrode 942A configured to sense when an elongate shaft 924 of the uterine manipulator is located in-situ in a desired position. A desired position (e.g., treatment position, surgical position, resection position, therapeutic position) can include, at least in part, a position of the split return electrode where a desired threshold of contact with tissue has been met or traversed. The desired threshold of contact can be a predetermined threshold of contact. These features and others are further described herein, particularly with respect to FIGS. 9-11.

The split return electrode 942A can have a first return electrode 944 and a second return electrode 946. The split return electrode 942A can be configured to be electrically coupled to the generator 940, such as a monopolar generator similar or the same as, electrosurgical generator 240 shown in FIGS. 2 and 3. The generator 940 can include an active output terminal 962, an active lead 964, a first lead 966A, a second lead 966B, and a return terminal 968.

The split return electrode 942A has the advantage that it can be used for return electrode monitoring (REM). The generator 940 circuitry is described with additional reference to FIG. 10. A REM system 970 including circuitry in the generator 940 can monitor contact area between the patient 1 and the first and second electrodes 944, 946 by monitoring one or more electrical properties of the first and second electrodes 944, 946. By monitoring signals transmitted to and received from the split return electrode 942A, the REM system 970 can prevent tissue damage caused by incomplete contact or a disruption in contact between the split return electrode 942A and the patient's tissue (e.g., cervix C, uterus U). If the REM system 970 determines from monitored electrical properties that contact with the patient 1 is not sufficient, the generator 940 can prevent delivery of energy to the active electrode 316A of the cutting device 316 (or alternatively 216A, 216).

The split return electrode 942A can be monitored by the generator 940 to determine the degree of contact with the patient 1. In one non-limiting example for the purposes of illustration, the REM system 970 can form a resonant system with the split return electrode 942A which can resonate at a specific interrogation frequency. The REM system 970 can detect a signal in response to a supplied drive signal (e.g., monitoring signal) at a predetermined clock frequency, such as from a controller 980 (FIG. 10). The REM system 970 thereafter can produce a voltage indicative of the resonations. As the impedance between the first return electrode 944 and the second return electrode changes 946, the resonance of the REM system 970 changes as well, this causes the amplitude to change. By monitoring changes in the amplitude, the REM system 970 can determine the magnitude of the impedance between the first electrode 944 and the second electrode 946 which reflects the level of contact of the first and second electrodes 944, 946 with the patient 1. In particular, the magnitude of the impedance can be indicative of the contact of the first electrode 944 with the internal portion of the uterus U and the contact of the second electrode 946 with the lumen L of the cervix C (FIG. 9). In some examples, each of the first electrode 944 and the second electrode 946 can be arranged to come in to contact with either or both of the cervix C and the uterus U.

In other examples, the REM system 970 in the generator 940 can measure not only the magnitude of the impedance but also voltage V, current I and phase ¢ with respect to frequency of the waveform. This allows the REM system 970 to measure a shift in frequency along with the amplitude shift. The shift in frequency can indicate a shift in reactance across the REM system 970. Reactance can provide a measurement of contact of the split return electrode 942A to the cervical C and uterine U tissue. As the split return electrode 942A is inserted into the patient's cervix C and uterus U, the reactance (e.g., capacitance) can change the resonance frequency of the REM system 970. A detection in the reactance can be used as an indicator of the amount of contact of the split return electrode 942A, and thereby the contact of the uterine manipulator 924 with the uterus U and cervix C. In some examples, this split return electrode 942A described with respect to FIG. 9, can be substituted in place of any of the other return electrodes described herein, such as with respect to the return electrodes of FIGS. 2-4. In other words, the return electrode members 242 in FIGS. 2 and 3 could incorporate the split return electrode 942A features.

As shown in FIG. 9, the split return electrode 942A can include a first electrode 944 and a second electrode 946. The second electrode 946 can be located proximal of the first electrode 944. The first or second electrodes 944, 946 (as well as any of the return electrodes described herein), can extend peripherally or circumferentially around the uterine manipulator 924, however, this is not required. In some examples, the split return electrode 942A need not encircle the uterine manipulator 924, or as applied to the examples of FIGS. 2-3, the split return electrode need not encircle the protrusion 258. The first electrode 944 can have a first surface area and the second electrode 946 can have a second surface area. In some examples, the first surface area and the second surface area can be equal or substantially equal. In the example of FIG. 9, the first surface area is larger than the second surface area, such as in a range at least 20-200% larger, and possibly more preferably 50-150% larger. This arrangement can result in a uterine manipulator 924 where the first electrode 944 can be configured to be located mostly or completely in the cervix C or the uterus U and the second electrode 946 can be configured to be located mostly or completely in the cervix C when the end effector 914 is positioned in-situ in a surgical position as shown in FIG. 9. In other examples, the first surface area can be smaller than the second surface area.

Further as shown in FIG. 9, the first electrode 944 can have a first longitudinal length L1 extending along a longitudinal path (may be longitudinal axis A1 but not required to be an axis) of the elongate shaft 924A, and the second electrode 946 can have a second longitudinal length L2 extending along the longitudinal path (may be longitudinal axis A1 but not required to be an axis). The first longitudinal length L1 can be equal to or substantially equal to the second longitudinal length L2. However, as shown in the example of FIG. 9, the first longitudinal length L1 can be greater than the second longitudinal length L2. In other examples, the first longitudinal length L1 can be less than the second longitudinal length L2.

The split return electrode 942A can return energy to the generator 940 and can also play a role in monitoring contact of the return electrode 942 with the tissue. In addition, the split return electrode 942A can provide other benefits that are not accomplished with conventional return electrodes, or conventional split return electrode pads. For example, the split return electrode 942A of FIG. 9, in conjunction with the generator 940 REM system 970 (e.g., circuitry), can also monitor the location of the end effector 914 and can determine when the uterine manipulator 924 or colpotomy cup 925 is in a desired position, such as being sufficiently or fully inserted into the patient 1, such as a distal end portion (e.g., a rim) of the cup fully or sufficiently delineating the vaginal fornices, or the split return electrode 942A being fully or sufficiently in contact with the tissue.

For example, the second return electrode 944 can be configured to contact the lumen L of the cervix C when the uterine manipulator 924 is inserted in-situ with the colpotomy cup 925 in contact with a target anatomy, such as the vaginal fornix VF, cervix C, cervical lumen L, cervical vaginal junction CVJ, or tissue proximate a cervix C (FIG. 1). In this arrangement, an electrical property, such as, but not limited to, impedance or reactance, can change depending on the position of the uterine manipulator 924 with respect to the anatomy of the patient 1. By monitoring the signals to and from the split return electrode 942A, the generator 940 can determine if the first and/or second electrode 944, 946 is in a desired position, such as in contact with the lumen L of the cervix C. Upon determining that the split return electrode 942A is in contact with the lumen L of the cervix C, the surgical generator 940 can allow a therapeutic energy to be delivered to the active electrode 316A (or in an alternate example, active electrode 216A). If, however, the first and/or second electrode 946 is determined to not be in contact with the lumen L of the cervix C, or if the electrical property, such as the impedance or reactance value does not meet or traverse a threshold value, the generator 940 can inhibit delivery of a therapeutic energy to the active electrode 316 (or in an alternate example active electrode 216A, see FIG. 9). Inhibiting the delivery of a therapeutic energy to the active electrode (316A or 216A) when the end effector 914 is not fully inserted reduces a risk of heating tissue proximate the split return electrode 942A above a desired temperature.

The generator 940 can include a user interface 960 to allow a user to control the generator 940, and to provide and an indication or display output to a user. In some examples the user interface 960 can include, but is not limited to, a display, input knobs, a keyboard, a touch screen, and audible, visual or tactile alarms. The user interface 960 can allow the user to adjust the power of the RF energy, waveform and other parameters to achieve the desired waveform for a particular type of tissue treatment.

FIG. 10 is a schematic block diagram of the surgical system 900 of FIG. 9 including the generator 940 and the connection with the patient 1 during use. While the schematic block diagram is described with respect to the end effector 914 of FIG. 9 including the integral cutting device 316 introduced in FIGS. 3 and 9, in some examples, the integral cutting device 316 of FIG. 9 can be omitted and replaced with the separate monopolar electrosurgical device 216 as described in FIG. 2 (shown in dotted line in FIG. 9). Regardless of whether the active electrode 316A is provided as an integral cutting device 316 or the alternate separate monopolar electrosurgical device 216 with active electrode 216A is provided, the active electrode 316A (or 216A) can be coupled to an active output terminal 962 of the generator 940. Further description is with reference to the cutting device being the integral cutting device 316 having active electrode 316A. Electrosurgical RF energy can be supplied to the active electrode 316A by the generator 940 via an active lead 964 (e.g., electrosurgical cable), which is connected to the active output terminal 962, allowing the active electrode 316A to treat the tissue. The energy is returned to the generator 940 through the split return electrode 942A via the first and second leads 966A, 966B to a return terminal 968. In addition, the generator 940 can be configured to monitor the degree of contact between the cervix C or uterus U to confirm that sufficient contact exists between the split return electrode 942A and the tissue to minimize the chances of tissue damage.

The generator 940 can include a controller 980, a DC power supply 982 and an RF output stage 984 which converts DC power into RF energy and delivers the RF energy to the active electrode 316A. The RF output can generate sinusoidal waveforms of high RF energy. The RF output can generate a plurality of waveforms having various suitable parameters for different types of electrosurgical treatments.

The controller 980 can include a processor 986 (e.g., processing circuitry) that is electrically connected to a memory 988 (e.g., non-transitory computer readable medium, RAM). The processor 986 can be operably connected to the power source 982 and the RF output stage 984 to allow the processor 986 to control the output of the generator 940 according to open loop or closed loop schemes.

The generator 940 can include the REM system 970 having a detection circuit 990 that is couplable to the first and second electrodes 944, 946 of the split return electrode 942A of the end effector 914. The end effector, 914, when vaginally inserted into the patient 1, can return the electrosurgical energy to the generator 940 from the first and second electrodes 944, 946 via first and second leads 966A and 966B. In at least one illustrative example, the first and second leads 966A and 966B may be coupled in one return line and can terminate at a secondary winding 995 of a transformer 992. The first and second leads 966A, 966B can be connected by capacitors 994 and 996. A return lead 998 can be coupled between capacitors 994 and 996 and can be configured to return the therapeutic electrosurgical energy to the RF output stage 984. The transformer 992 can also include a primary winding electrically connected to the detection circuit 990. The REM system 970 can also include sensors such as a voltage sensor 991 or a current sensor 993 on the primary side of the transformer 992.

Components of the REM system 970 such as the transformer 992, the first and second electrodes 944, 946, the capacitors 994, 996 and the detection circuit 990 can form a resonant system which is adapted to resonate at a specific interrogation frequency from the controller 980. For example, the controller 980 can provide a drive signal, REM CLK, at the specific interrogation frequency to the detection circuit 990. The drive signal, REM CLK is a clock signal generated by the controller 980 at the desired frequency. The drive signal can be a constant, physiologically benign waveform that the detection circuit 990 transmits to the first electrode 944. The drive signal can then passe through the patient and is collected by the second electrode 946 and returned to the detection circuit 990. The detection circuit 990 can then measure a response signal to the drive signal and monitor the changes in the received response signal.

The response signal (e.g., returning drive signal) is modified by the impedance of the first electrode 944 and the second electrode 946. As the impedance between the first electrode 944 and the second electrode 946 changes due to movement of the end effector 914 along a vaginal path, the resonance of the detection circuit 990 with respect to other components changes as well. The change in the resonance, in turn, affects change in amplitude of the drive signal. Thus, the detection between the first and second electrodes 944, 946 by monitoring changes in amplitude of the drive signal. The detection circuit 990 then supplies the impedance measurement to the controller 980, which determines whether the impedance is within a predetermined range. If the impedance is out of range or traverses one or more thresholds, which can indicate the end effector 914 is in or out of position, or does not have desired contact with the tissue, the controller 980 can send an instruction to the user interface 960 to alert the user via an alarm or indicator. The controller 980 can also adjust an output of the generator 940, such as to allow delivery of a therapeutic energy if the end effector 914 is in a treatment location or in sufficient contact with tissue, or can inhibit delivery of a therapeutic energy to the active electrode 916A of the cutting device 916 if the end effector 914 is not in a desired position such as a treatment position or location (FIG. 9). In some examples the controller 980 can send an inquiry to the user as to whether they want to allow delivery of a therapeutic energy based, at least in part, on the alarm or indicator (e.g., an operator override).

The above-described operation of the detection circuit 990 using a single frequency signal allows for measuring a relative change in the magnitude of impedance. In other examples, the REM system 970 can monitor the split return electrode 942A by any means known in the art. In one such other example, the detection circuit 990 can track the frequency response of the REM system 970 and determine a complex impedance thereacross. Electrical impedance can describe not only the relative magnitudes of the voltage and current, but also the relative phases. Impedance is a "complex" value that can include a part related to a resistance and a part related to reactance. The generator 940 can use any suitable detection circuit 990 to monitor the split return electrode 942A to determine if the end effector 914 is fully inserted into the vaginal canal.

Figure 11:
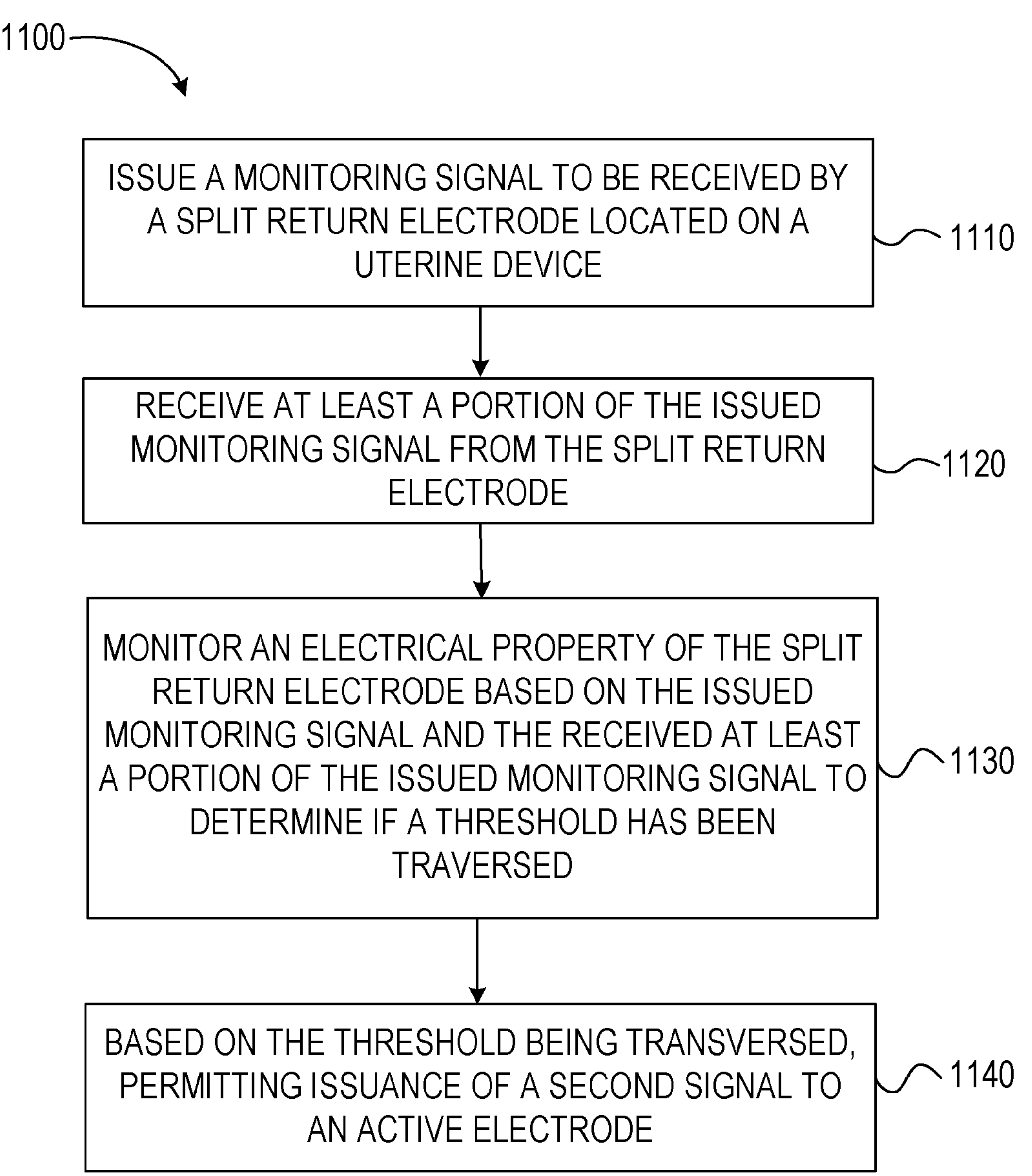
FIG. 11 is a flow chart for performing a surgical method using the end effector of FIG. 9 and the surgical system of FIG. 10, in accordance with at least one example.

While the memory 988 is illustrated in an example embodiment to be a single machine readable medium, the term "machine-readable medium" may include a single medium or multiple media (e.g., a centralized or distributed database, and/or associated caches and servers) that store the one or more instructions for performing methods of the surgical system 900 of FIGS. 9 and 10, and such as for performing a method 1100 as described in FIG. 11. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

FIG. 11 is a flow chart for a method of determining an in-situ position of a vaginally-insertable medical device, and in some steps, performing a related treatment method using the surgical system 900 of FIGS. 9 and 10. The method 1100 can be used to place a uterine device or perform a tissue resection procedure, including but not limited to, a colpotomy. The method 1100 can be performed by the generator 940, such as by the controller 980 including the processor 986 and memory 988.

In some examples, aspects of any of the end effectors 14, 214, 314 and 914 and aspects of any of the cutting devices 216 or 316 can be used with the method 1100, but the method 1100 can also be used with other surgical systems. Likewise, the surgical system 900 of FIGS. 9 and 10 can be used with other methods. The example methods of the disclosure are particularly well-suited for procedures such as laparoscopic procedures with limited visibility of the tissue to be resected and adjacent anatomy.

Step 1110 can include, issuing a drive signal (e.g., monitoring signal) to be received by a split return electrode located on an end effector such as a uterine device.

Step 1020 can include, receiving a returned drive signal (e.g., at least a portion of the issued drive signal from the split return electrode (e.g., after the drive signal has passed through the tissue of the patient).

Step 1030 can include, monitoring an electrical property of the split return electrode based on the issued drive signal and the returned drive signal to determine if the electrical property is within a predetermined range or has traversed a threshold. In some examples, the range or threshold can indicate that an end effector is fully inserted, not inserted, incompletely inserted, incorrectly inserted or that the location is undeterminable. Any number of ranges or thresholds to communicate a variety of conditions of the location and position of the end effector may be provided. The monitored electrical property can include any suitable electrical property, such as but not limited to impedance, reactance, voltage, current or phase.

Step 1040 can include, based on the electrical property traversing a threshold or achieving a predetermined range, the method can include permitting issuance of a second signal to an active electrode. The second signal can be a tissue treating signal.

Other steps of the method 1100 can include, based at least in part on the monitored electrical property traversing the threshold or entering the predetermined range, issuing an indication signal to an indicator to indicate that the uterine device is in a desired position (e.g., predetermined position, treatment position, surgical position, resection position, therapeutic position, a position of the split return electrode where a desired threshold of contact with tissue has been met or traversed). The desired threshold of contact can be a predetermined threshold of contact.

Variations of method 1100 are not limited to colpotomy procedures, method 1100 can be used for directing in-situ guidance of an end effector in other procedures to determine if an end effector is located in a treatment position. For example, such as determining if a uterine ablation device is inserted in-situ.

Figure 12:
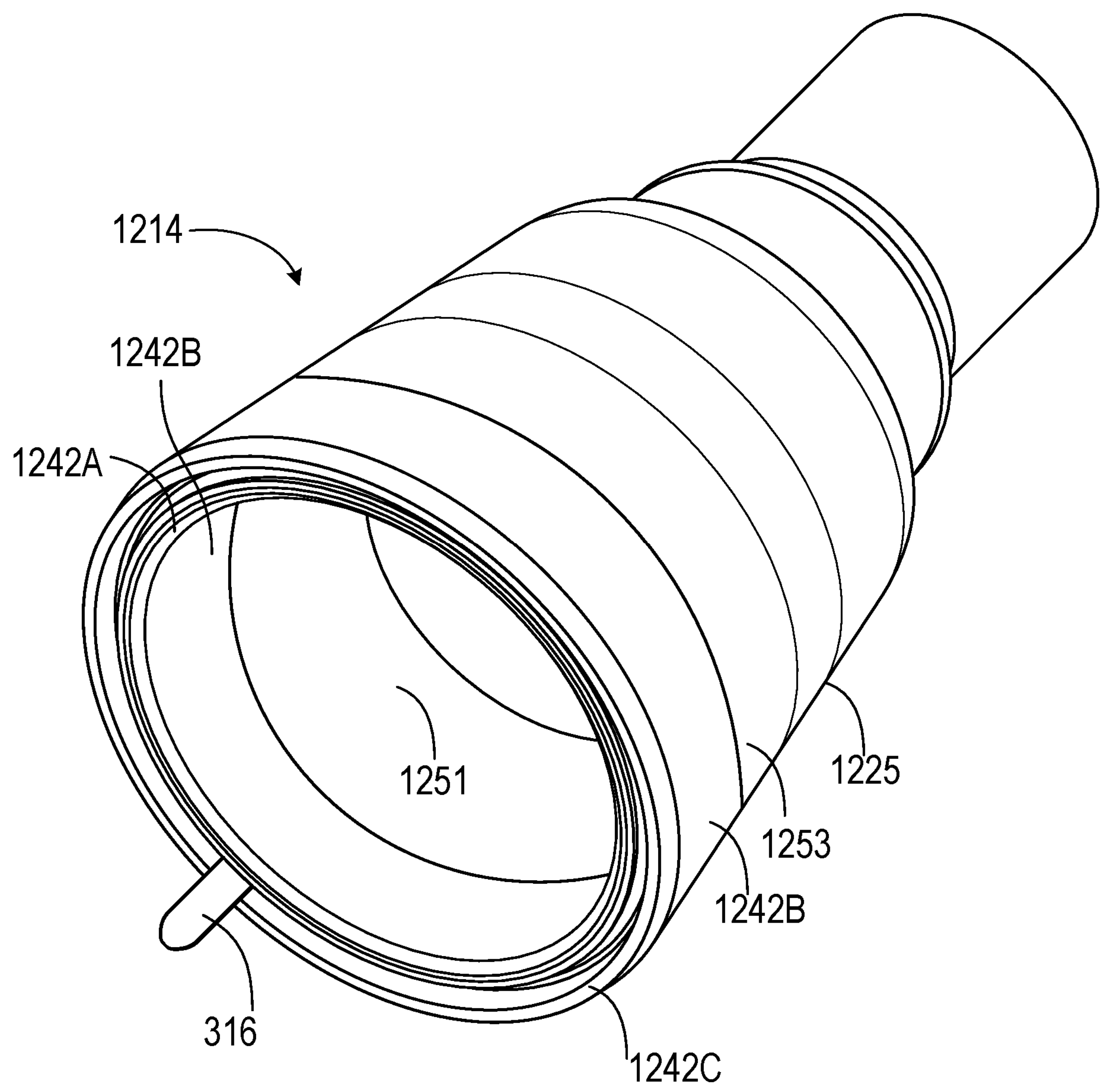
FIG. 12 is schematic illustration of an isometric view of fourth example of an end effector including a return electrode member, in accordance with at least one example.

FIG. 12 is schematic illustration of an isometric view of fourth example of an end effector 1214 including a return electrode member 1242. In addition to the return electrode member locations described in FIGS. 1-10, the return electrode member 1242 can be located on an inner surface 1251 of a colpotomy cup 1225 so as to make contact with an outer/lateral portion of the cervix C when vaginally-inserted and located proximate the cervical-vaginal junction (CVJ, FIG. 1) in an in-situ treatment position.

In other words, the colpotomy cup 1225 can form a cut guide extending from a proximal end to a distal end and can include a perimeter return electrode 1242 around the opening, wherein the perimeter return electrode 1242 can be configured to be electrically connected to an electrosurgical generator (e.g., 240 FIG. 4; 940, FIG. 9). Any aspects of the return electrode members described herein can be applied to a return electrode member 1242 located on the inner surface 1227 of the colpotomy cup 1225. In some examples a return electrode member 1242B can be located on an outer surface 1253 of the colpotomy cup 1225 or on a distal end of the colpotomy cup, such as on the rim as illustrated by return electrode member 1242C.

The benefits of the systems and methods of the present disclosure can include: 1) improved location for a neutral return electrode for surgeries of the abdominal cavity, such as procedures of the uterus; 2) improved accuracy in seating a colpotomy cup against a uterus or ensuring a uterine manipulator is fully inserted; and 3) improved tissue resection devices that reduce the likelihood of inadvertent injury to adjacent tissues, such as injury to a bowel or bladder in a colpotomy procedure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

VARIOUS NOTES AND EXAMPLES

Example 1 is a uterine manipulator comprising: an elongate shaft including a distal portion configured to be inserted into a uterus through a lumen of a cervix; and a split return electrode coupled to the elongate shaft, wherein the split return electrode is configured to be electrically coupled to an electrosurgical generator.

In Example 2, the subject matter of Example 1 includes, wherein the split return electrode is configured to sense when the elongate shaft is located in a treatment position.

In Example 3, the subject matter of Examples 1-2 includes, wherein the split return electrode comprises a first electrode and a second electrode, and wherein the second electrode is located proximal of the first electrode.

In Example 4, the subject matter of Examples 1-3 includes, wherein the split return electrode comprises a first electrode and a second electrode, and wherein the first electrode has a first surface area and the second electrode has a second surface area, wherein the first surface area is larger than the second surface area.

In Example 5, the subject matter of Examples 1~4 includes, wherein the split return electrode comprises a first electrode located distal of a second electrode, and wherein the first electrode has a first longitudinal length extending along a longitudinal path of the elongate shaft, and wherein the second electrode has a second longitudinal length extending along the longitudinal path, and wherein the first longitudinal length is greater than the second longitudinal length.

In Example 6, the subject matter of Examples 1-5 includes, a colpotomy cup, wherein the split return electrode comprises a first electrode and a second electrode, and wherein the second electrode is configured to contact the lumen of the cervix when the distal portion is inserted in-situ with the colpotomy cup in contact with the cervix.

Example 7 is a method of determining an in-situ position of a vaginally-insertable uterine device, the method comprising: issuing a drive signal to be received by a split return electrode located on the uterine device; receiving at least a portion of the issued drive signal from the split return electrode; monitoring an electrical property of the split return electrode based on the issued drive signal and the received at least a portion of the issued drive signal to determine if a threshold has been traversed; and based at least in part on the threshold being traversed, permitting issuance of a second signal to an active electrode.

In Example 8, the subject matter of Example 7 includes, wherein based at least in part on the monitored electrical property traversing the threshold, issuing an indication signal to a user interface to indicate that the uterine device is in a treatment position.

In Example 9, the subject matter of Examples 7-8 includes, wherein the split return electrode includes a first electrode and a second electrode, and wherein the first electrode is located distal of a second electrode along an elongate shaft of the uterine device.

In Example 10, the subject matter of Examples 7-9 includes, wherein monitoring the electrical property includes monitoring an impedance of the split return electrode.

In Example 11, the subject matter of Examples 7-10 includes, wherein the uterine device is a uterine manipulator.

In Example 12, the subject matter of Examples 7-11 includes, wherein the uterine device is a colpotomy cup device.

Example 13 is a tissue resection system comprising: a uterine manipulator including an elongate shaft having a distal portion configured to be inserted into a uterus through a lumen of a cervix; a split return electrode coupled to the elongate shaft, the split return electrode having a first electrode and a second electrode, the split return electrode configured to be electrically coupled to the electrosurgical generator; a colpotomy cup coupled to the elongate shaft, the colpotomy cup configured to be positioned in-situ around a cervix, wherein a distal portion of the colpotomy cup is configured to delineate a target tissue to be treated; and a cutting device including an active electrode to treat the target tissue, the cutting device configured to be electrically connected to an output of an electrosurgical generator.

In Example 14, the subject matter of Example 13 includes, wherein the colpotomy cup is configured to be delivered vaginally to a first surface of the target tissue and the cutting device is configured to be delivered laparoscopically to a second surface of the target tissue opposite the first surface.

In Example 15, the subject matter of Examples 13-14 includes, wherein the cutting device is coupled to the colpotomy cup and is actuatable to move along a periphery of the colpotomy cup to treat the target tissue.

In Example 16, the subject matter of Examples 13-15 includes, an electrosurgical generator, wherein the electrosurgical generator is configured to: issue a drive signal to the split return electrode; receive at least a portion of the issued drive signal from the split return electrode; monitor an electrical property of the split return electrode based on the issued drive signal and the received at least a portion of the issued drive signal to determine if a threshold has been traversed; and based at least in part on the threshold being traversed, permitting issuance of a second signal to an active electrode.

Example 17 is an end effector of a tissue treatment device comprising: a uterine manipulator including an elongate shaft having a distal end portion, wherein the distal end portion is configured to be inserted into a lumen of a cervix; and a colpotomy cup coupled to the uterine manipulator, the colpotomy cup comprising: a cut guide having an outer wall portion and a base portion supporting the outer wall portion, the outer wall portion configured to surround at least a portion of the cervix, the outer wall portion extending from a first proximal end portion to a first distal end portion along a longitudinal path; and a protrusion extending distally away from the base portion, the protrusion laterally spaced away from the outer wall portion and extending along the longitudinal path, wherein the protrusion is configured to be inserted into a lumen of the cervix, and wherein the protrusion includes, a return electrode member that is configured to be electrically connected to an electrosurgical generator.

In Example 18, the subject matter of Example 17 includes, wherein the return electrode member comprises an anchor, wherein the anchor is configured to inhibit egress of a distal portion of the anchor through the lumen of the cervix when positioned in-situ.

In Example 19, the subject matter of Examples 17-18 includes, wherein the return electrode member is actuatable to change from a first state to a second state, wherein in the first state, the return electrode member is configured to be inserted into the lumen of the cervix and wherein in the second state, the return electrode member is configured to inhibit removal of the inserted return electrode member proximally relative to the lumen of the cervix.

Example 20 is an end effector of a tissue treatment device comprising: a uterine manipulator including an elongate shaft extending from a proximal end portion to a distal end portion, wherein the distal end portion is configured to be inserted into a lumen of a cervix; a colpotomy cup coupled to the elongate shaft; and a return electrode member coupled to the colpotomy cup, the return electrode member configured to be electrically connected to an electrosurgical generator, wherein the return electrode member is actuatable to change from a first state to a second state, wherein in the first state, the return electrode member is configured to be inserted into the lumen of the cervix and wherein in the second state, the return electrode member is configured to inhibit removal of the inserted return electrode member proximally relative to the lumen of the cervix.

In Example 21, the subject matter of Example 20 includes, wherein the colpotomy cup further comprises: an outer wall portion configured to surround at least a portion of the cervix, the outer wall portion extending from a first proximal end portion to a first distal end portion along a longitudinal path; and a base portion coupled the outer wall portion, wherein the return electrode member is laterally spaced away from the outer wall portion and is coupled to the outer wall portion by the base portion.

In Example 22, the subject matter of Examples 20-21 includes, wherein the first state is a collapsed state and wherein the second state is an expanded state.

In Example 23, the subject matter of Examples 20-22 includes, wherein the return electrode member has a first size in a first state and a second size in a second state, and wherein the second size is greater than the first size.

In Example 24, the subject matter of Examples 20-23 includes, wherein there return electrode member has a first diameter in a first state and a second diameter in a second state.

In Example 25, the subject matter of Examples 20-24 includes, wherein the return electrode member comprises an inflatable balloon.

In Example 26, the subject matter of Examples 20-25 includes, wherein the return electrode member comprises barbs.

In Example 27, the subject matter of Examples 20-26 includes, wherein the return electrode member comprises a slotted tube that is actuatable to change from the first state to the second state.

In Example 28, the subject matter of Examples 20-27 includes, wherein the return electrode member comprises at least a portion of a tapered cylinder configured to anchor the return electrode member relative to the lumen of the cervix.

Example 29 is an end effector of a tissue treatment device comprising: an elongate shaft extending from a proximal end portion to a distal end portion, wherein the proximal end portion is manipulatable by a user or a machine to deliver the distal end portion to a treatment site, and wherein the distal end portion is configured to be inserted into a lumen of a cervix; and a return electrode coupled to the distal end portion, wherein the return electrode is configured to be electrically coupled to an electrosurgical generator, and wherein the return electrode is configured to inhibit proximal movement of the elongate shaft relative to the lumen of the cervix when the return electrode is positioned in the lumen of the cervix.

In Example 30, the subject matter of Example 29 includes: a cutting device including an active electrode; and a cutting guide coupled to the elongate shaft, wherein the cutting guide is configured to support the cutting device.

In Example 31, the subject matter of Examples 29-30 includes, a first cut guide having a first distal peripheral portion; a second cut guide having a second distal peripheral portion, the second cut guide located around the first cut guide; and a cutting device including an active electrode located between the first cut guide and the second cut guide, wherein the cutting device is moveable relative to at least one of the first distal peripheral portion and the second distal peripheral portion.

Example 32 is a tissue resection system comprising: a cutting device including an active electrode configured to receive a signal from surgical generator; and a cut guide configured to be inserted into a patient, the cut guide extending from a proximal end to an opening at a distal end, wherein the distal end includes, a perimeter return electrode around the opening, wherein the perimeter return electrode is configured to be electrically connected to an electrosurgical generator.

Example 33 is at least one machine-readable medium including instructions that, when executed by processing circuitry, cause the processing circuitry to perform operations to implement of any of Examples 1-32.

Example 34 is an apparatus comprising means to implement of any of Examples 1-32.

Example 35 is a system to implement of any of Examples 1-32.

Example 36 is a method to implement of any of Examples 1-32.

What is claimed is:

1. A method of determining an in-situ position of a vaginally-insertable uterine device, the method comprising:

using an electrosurgical generator, issuing a drive signal to a first return electrode, wherein the uterine device comprises a colpotomy cup comprising an outer wall portion, a base, and a protrusion configured for receiving an elongate shaft and the first return electrode is arranged on the protrusion;

using the electrosurgical generator, receiving a portion of the issued drive signal from a second return electrode arranged on the protrusion;

using a processor of the electrosurgical generator, monitoring an electrical property between the first and second return electrodes based on the issued drive signal and the received portion of the issued drive signal to determine if a threshold has been traversed; and based at least in part on the threshold being traversed, using a processor to permit issuance of a second signal to an active electrode.

2. The method of claim 1, wherein based at least in part on the monitored electrical property traversing the threshold, issuing an indication signal to a user interface to indicate that the uterine device is in a treatment position.

3. The method of claim 1, wherein the first return electrode is located distal of the second return electrode along the elongate shaft of the uterine device.

4. The method of claim 3, wherein monitoring the electrical property includes monitoring an impedance between the first return electrode and the second return electrode.

5. The method of claim 3, wherein monitoring the electrical property includes monitoring voltage, current, and phase.

6. The method of claim 3, further comprising inserting the elongate shaft into a patient's cervix and uterus prior to issuing the drive signal.

7. The method of claim 3, wherein the first return electrode and the second return electrode extend circumferentially around the elongate shaft.

8. The method of claim 3, wherein the first return electrode has a first surface area and the second return electrode has a second surface area.

9. The method of claim 8, wherein the first surface area is larger than the second surface area.

10. The method of claim 9, wherein the first surface area is from 20% to 200% larger than the second surface area.

11. The method of claim 10, wherein the first surface area is from 50% to 150% larger than the second surface area.

12. The method of claim 3, wherein the first return electrode has a first longitudinal length and the second return electrode has a second longitudinal length.

13. The method of claim 12, wherein the first longitudinal length is greater than the second longitudinal length.

14. The method of claim 3, wherein issuing the drive signal comprises delivering a monitoring signal at a predetermined clock frequency to establish resonations.

15. The method of claim 14, further comprising producing a voltage indicative of the resonations.

16. The method of claim 15, further comprising monitoring changes in an amplitude of the resonations.

17. The method of claim 16, further comprising determining a magnitude of impedance between the first return electrode and the second return electrode based on the changes in the amplitude.

18. The method of claim 1, wherein the second signal comprises therapeutic energy being delivered to the active electrode.

19. A method of determining an in-situ position of a vaginally-insertable uterine device, the method comprising:

inserting the uterine device into the vagina of a patient;

advancing the uterine device to the cervix and arranging a first return electrode of the uterine device and a second return electrode of the uterine device within the cervix;

using an electrosurgical generator, issuing a first signal to the first return electrode;

using the electrosurgical generator, receiving a portion of the issued first signal from the second return electrode;

using a processor of the electrosurgical generator, monitoring an electrical property of the first and second return electrodes based on the issued first signal and the received portion of the issued first signal to determine if a threshold has been traversed to confirm that the first and second return electrodes are in contact with an inner surface of the cervix; and based at least in part on the threshold being traversed, using a processor to permit issuance of a second signal to an active electrode.

* * * * *